US009428758B2

(12) United States Patent
Tumer et al.

(10) Patent No.: US 9,428,758 B2
(45) Date of Patent: Aug. 30, 2016

(54) PLANT GENES THAT CONFER RESISTANCE TO TRICHOTHECENE MYCOTOXINS AND FUSARIUM HEAD BLIGHT

(71) Applicant: Rutgers, The State University of New Jersey, New Brunswick, NJ (US)

(72) Inventors: Nilgun Ereken Tumer, Belle Mead, NJ (US); John Edward McLaughlin, Bernardsville, NJ (US); Mohamed Anwar Bin-Umer, Highland Park, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 573 days.

(21) Appl. No.: 13/693,024

(22) Filed: Dec. 3, 2012

(65) Prior Publication Data

US 2014/0013470 A1    Jan. 9, 2014

Related U.S. Application Data

(60) Provisional application No. 61/566,095, filed on Dec. 2, 2011.

(51) Int. Cl.
*C12N 15/82* (2006.01)
*C07K 14/415* (2006.01)

(52) U.S. Cl.
CPC ......... *C12N 15/8241* (2013.01); *C07K 14/415* (2013.01); *C12N 15/8282* (2013.01)

(58) Field of Classification Search
None
See application file for complete search history.

(56) References Cited

PUBLICATIONS

Molina and Garcia-Olmedo (1997) Plant J. 12: 669-675.*
Molina et al (1993) FEBS 316: 119-122.*
Molina and Garcia-Olmedo (1993) Plant J. 4: 983-991.*
Ueno et al (1975) App. Micrbiol. 30: 4-9.*
Sels et al (2008) Plant Physiol. and Biochem. 46: 941-950.*
Bischoff et al, (2010) Plant Physiol. 153: 590-602.*
Foroud, Trichothecenes in cereal grains. Int J Mol Sci. 2009; 10: 147-173.
McMullen et al. Scab of wheat and barley: A re-emerging disease of devastating impact. Plant Dis. 1997; 81: 1340-1348.
Desjardins et al., Trichothecene biosynthesis in *Fusarium* species—Chemistry, genetics, and significance. Microbiol Rev. 1993; 57: 595-604.
McCormick et al., Trichothecene triangle: toxins, genes, and plant disease. Phytochemicals, Plant Growth, and the Environment; 2013 Springer. pp. 1-17.
McMullen et al., A unified effort to fight an enemy of wheat and barley: Fusarium Head Blight. Plant Dis. 2012; 96: 1712-1728.
Buerstmayr et al., QTL mapping and marker-assisted selection for Fusarium head blight resistance in wheat: a review. Plant Breed. 2009; 128: 1-26.
Ansari et al., Light influences how the fungal toxin deoxynivalenol affects plant cell death and defense responses. Toxins (Basel). 2014; 6: 679-692.
Wegulo et al., Effects of integrating cultivar resistance and fungicide application on Fusarium head blight and deoxynivalenol in winter wheat. Plant Dis. 2011; 95: 554-560.
Proctor et al., Reduced virulence of Gibberella zeae caused by disruption of a trichothecene toxin biosynthetic gene. Mol Plant Microbe Interact. 1995; 8: 593-601.
Desjardins et al., Reduced virulence of trichothecene-nonproducing mutants of Gibberella zeae in wheat field tests. Molecular Plant Microbe Interact. 1996; 9: 775-781.
Jansen et al., Infection patterns in barley and wheat spikes inoculated with wild-type and trichodiene synthase gene disrupted Fusarium graminearum. Proc Natl Acad Sci USA. 2005; 102: 16892-16897.
Fried et al., Cloning of yeast gene for trichodermin resistance and ribosomal protein L3. Proc Natl Acad Sci USA. 1981; 78: 238-242.
Wickner et al., Ribosomal protein L3 is involved in replication or maintenance of the killer double-stranded RNA genome of *Saccharomyces cerevisiae*. Proc Natl Acad Sci USA. 1982; 79: 4706-4708.
Cundliffe et al., Mechanism of inhibition of eukaryotic protein synthesis by trichothecene fungal toxins. Proc Natl Acad Sci USA. 1974; 71: 30-34.
Di et al., Expression of a truncated from of yeast ribosomal protein L3 in transgenic wheat improves resistance to Fusarium head blight. Plant Sci. 2010; 178: 374-380.
Harris et al., A modified Rpl3 gene from rice confers tolerance of the Fusarium graminearum mycotoxin deoxynivalenol to transgenic tobacco. Mol Plant Pathol. 2001; 58: 173-181.
Di et al., Turner NE. Expression of a truncated form of ribosomal protein L3 confers resistance to pokeweed antiviral protein and the Fusarium mycotoxin deoxynivalenol. Mol Plant Microbe Interact. 2005; 18: 762-770.
Shin et al., Transgenic Arabidopsis thaliana expressing a barley UDP-glucosyltransferase exhibit resistance to the mycotoxin deoxynivalenol. J Exp Bot. 2012; 63: 4731-4740.
Lemmens et al., The ability to detoxify the mycotoxin deoxynivalenol colocalizes with a major quantitative trait locus for Fusarium head blight resistance in wheat. Mol Plant Microbe Interact. 2005; 18: 1318-1324.
Wu et al., Public health impacts of foodborne mycotoxins. Annu Rev Food Sci Technol. 2014; 5: 351-372.
Arunachalam et al., Trichothecene toxicity in eukaryotes: cellular and molecular mechanisms in plants and animals. Toxicol Lett. 2013; 217: 149-158.
Petska et al., Deoxynivalenol-induced proinflammatory gene expression: mechanisms and pathological sequelae. Toxins (Basel). 2010; 2: 1300-1317.
Desmond et al., The Fusarium mycotoxin deoxynivalenol elicits hydrogen peroxide production, programmed cell death and defence responses in wheat. Mol Plant Pathol. 2008; 9: 435-445.
Gardiner et al., Transcriptome analysis of the barley-deoxynivalenol interaction: evidence for a role of glutathione in deoxynivalenol detoxification. Mol Plant Microbe Interact. 2010; 23: 962-976.

(Continued)

*Primary Examiner* — Russell Kallis
(74) *Attorney, Agent, or Firm* — Kathleen D. Rigaut; Dann, Dorfman, Herrell & Skillman

(57) ABSTRACT

Compositions and methods are disclosed for modulating disease resistance in plants.

11 Claims, 14 Drawing Sheets

(56) References Cited

PUBLICATIONS

Schweiger et al., Transcriptomic characterization of two major Fusarium resistance quantitative trait loci (QTLs), Fhb1 and Qfhs. ifa-5A, identifies novel candidate genes. Mol Plant Pathol. 2013; 14: 772-785.

Walter et al., Transcript profiling of the phytotoxic response of wheat to the Fusarium mycotoxin deoxynivalenol. Mycotoxin Res. 2011; 27: 221-230.

Ding et al., Resistance to hemi-biotrophic F. graminearum infection is associated with coordinated and ordered expression of diverse defense signaling pathways. PLoS One. 2011; 6(4): e19008.

Audenaert et al., Hydrogen peroxide induced by the fungicide prothioconazole triggers deoxynivalenol (DON) production by Fusarium graminearum. BMC Microbiol. 2010; 10: 112.

Gardiner et al., Early activation of wheat polyamine biosynthesis during Fusarium head blight implicates putrescine as an inducer of trichothecene mycotoxin production. BMC Plant Biol. 2010; 10: 289.

McLaughlin et al., A genome-wide screen in *Saccharomyces cerevisiae* reveals a critical role for the mitochondria in the toxicity of a trichothecene mycotoxin. Proc Nat Acad Sci USA. 2009; 106: 21883-21888.

Bin-Umer et al., Trichothecene mycotoxins inhibit mitochondrial translation—implication for the mechanism of toxicity. Toxins (Basel). 2011; 3: 1484-1501.

Bin-Umer et al., Elimination of damaged mitochondria through mitophagy reduces mitochondrial oxidative stress and increases tolerance to trichothecenes. Proc Natl Acad Sci USA. 2014; 111: 11798-11803.

Weigel et al., Activation tagging in Arabidopsis. Plant Physiol. 2000; 122: 1003-1013.

Boutrot et al., Genome-wide analysis of the rice and Arabidopsis non-specific lipid transfer protein (nsLtp) gene families and identification of wheat nsLtp genes by EST data mining. BMC Genomics. 2008; 9: 86.

Earley et al., Gateway-compatible vectors for plant functional genomics and proteomics. Plant J. 2006; 45: 616-629.

Zhang et al., Agrobacterium-mediated transformation of Arabidopsis thaliana using the floral dip method. Nature Protocols. 2006; 1: 641-646.

Mari et al., Mitochondrial glutathione, a key survival antioxidant. Antioxid Redox Signal. 2009; 11: 2685-2700.

Zhang et al., Aberrant gene expression in the Arabidopsis SULTR1;2 mutants suggests a possible regulatory role for this sulfate transporter in response to sulfur nutrient status. Plant J. 2014; 77: 185-197.

Gossett et al., Antioxidant response to NaCl stress in a control and an NaCl-tolerant cotton cell line grown in the presence of paraquat, buthionine sulfoximine, and exogenous glutathione. Plant Physiol. 1996; 112: 803-809.

Kader et al., Lipid-transfer proteins in plants. Ann Rev Plant Physiol Plant Mol Biol. 1996; 47: 627-654.

Yeats et al., The biochemistry and biology of extracellular plant lipid-transfer proteins (LTPs). Protein Sci. 2008; 17: 191-198.

Sarowar et al., Overexpression of lipid transfer protein (LTP) genes enhances resistance to plant pathogens and LTP functions in long-distance systemic signaling in tobacco. Plant Cell Rep. 2009; 28: 419-427.

Jung et al., Three pathogen-inducible genes encoding lipid transfer protein from pepper are differentially activated by pathogens, abiotic, and environmental stresses. Plant Cell Environ. 2003; 26: 915-928.

Maldonado et al., A putative lipid transfer protein involved in systemic resistance signalling in Arabidopsis. Nature. 2002; 419: 399-403.

Champigny et al., Long distance movement of DIR1 and investigation of the role of DIR1-like during systemic acquired resistance in Arabidopsis. Front Plant Sci. 2013; 4: 230.

Nomura et al., Chloroplast-mediated activation of plant immune signalling in Arabidopsis. Nat Commun. 2012; 3: 926.

Zurbriggen et al., Chloroplast-generated reactive oxygen species play a major role in localized cell death during the non-host interaction between tobacco and *Xanthomonas campestris* pv. *vesicatoria*. Plant J. 2009; 60: 962-973.

Chen et al., The Arabidopsis Paraquat Resistant2 gene encodes an S-nitrosoglutathione reductase that is a key regulator of cell death. Cell Res. 2009; 19: 1377-1387.

Bushnell et al., Effects of deoxynivalenol on content of chloroplast pigments in barley leaf tissues. Phytopathol. 2010; 100: 33-41.

Xing et al., Reactive oxygen species promote chloroplast dysfunction and salicylic acid accumulation in fumonisin B1-induced cell death. FEBS Lett. 2013; 587: 2164-2172.

Noctor et al., Glutathione in plants: an integrated overview. Plant Cell Environ. 2012; 35: 454-484.

Kluger et al., Stable isotopic labellingassisted untargeted metabolic profiling reveals novel conjugates of the mycotoxin deoxynivalenol in wheat. Anal Bioanal Chem. 2013; 405: 5031-5036.

Poppenberger et al., Detoxification of the Fusarium mycotoxin deoxynivalenol by a UDP-glucosyltransferase from Arabidopsis thaliana. J Biol Chem. 2003; 278: 47905-47914.

Fruhmann et al., Methylthiodeoxynivalenol (MTD): insight into the chemistry, structure and toxicity of thia-Michael adducts of trichothecenes. Org Biomol Chem. 2014; 12: 5144-5150.

Bertiller et al., Masked mycotoxins: a review. Mol Nutr Food Res. 2013; 57: 165-186.

Poole et al., Discovering mechanisms of signaling-mediated cysteine oxidation. Curr Opin Chem Biol. 2008; 12: 18-24.

Mahajan et al., Tumor-suppressive maspin functions as a reactive oxygen species scavenger: Importance of cysteine residues. J Biol Chem. 2013; 288: 11611-11620.

De Coninck et al., Mining the genome of Arabidopsis thaliana as a basis for the identification of novel bioactive peptides involved in oxidative stress tolerance. J Exp Bot. 2013; 64: 5297-5307.

Singer et al., High-throughput TAIL-PCR as a tool to identify DNA flanking insertions. Methods Mol Biol. 2003; 236: 241-272.

Desjardins et al., Structure-activity relationships of trichothecene toxins in an Arabidopsis thaliana leaf assay. J Agric Food Chem. 2007; 55: 6487-6492.

Kluger et al., Biotransformation of the mycotoxin deoxynivalenol in Fusarium resistant and susceptible near isogenic wheat lines. PLoS One. 2015; 10(3): e0119656.

* cited by examiner

Figure 1
Chr. 5
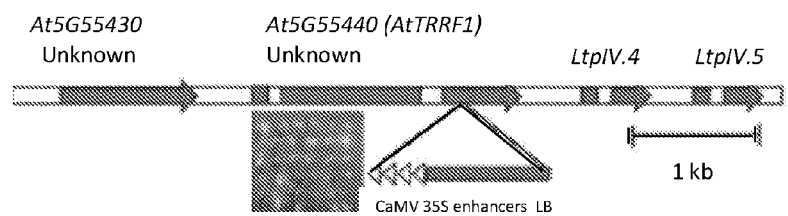
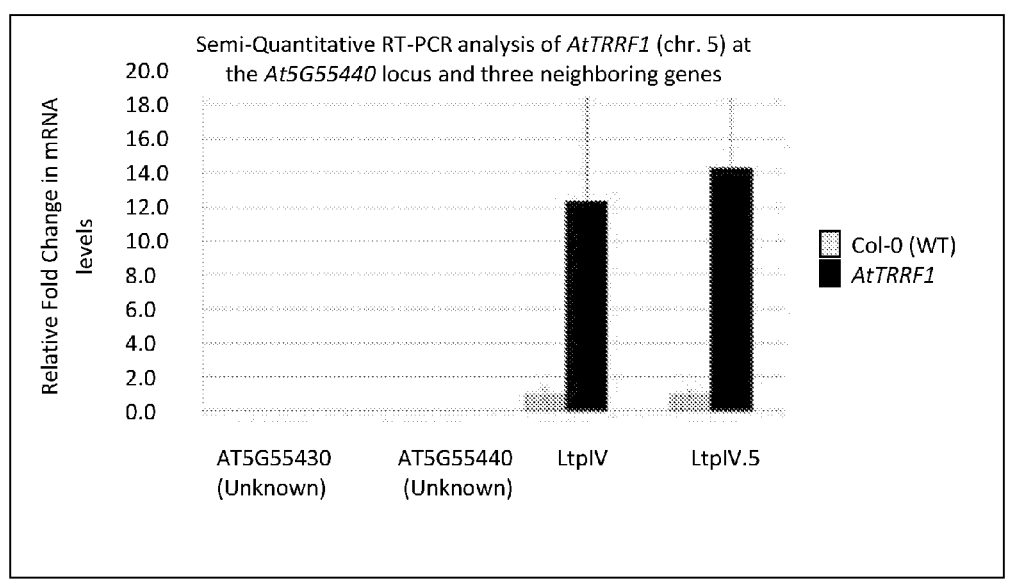

Figure 2. Col-0 and LtpIV.4's expression data using anti-His antibody
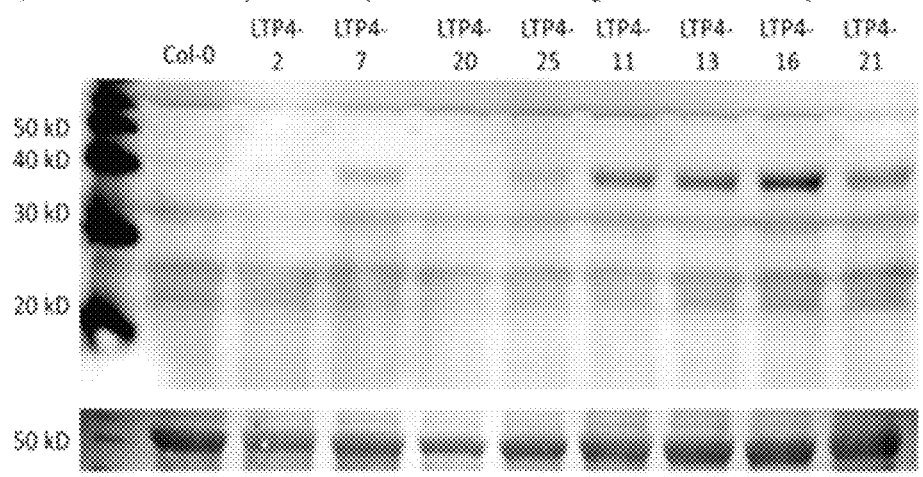
Reprobed with polyclonal antibody raised against SAT1
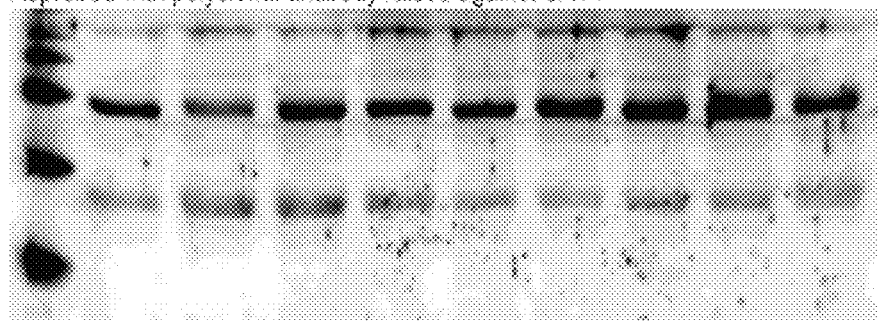

Figure 12.
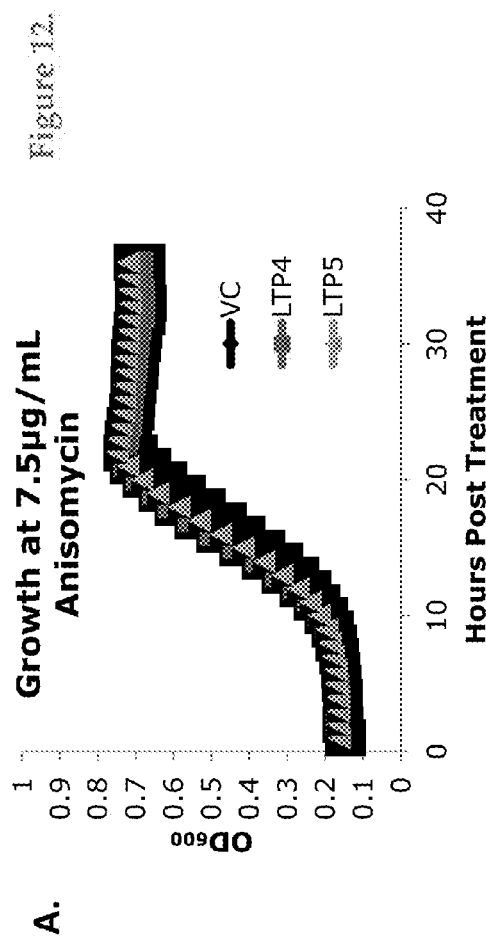
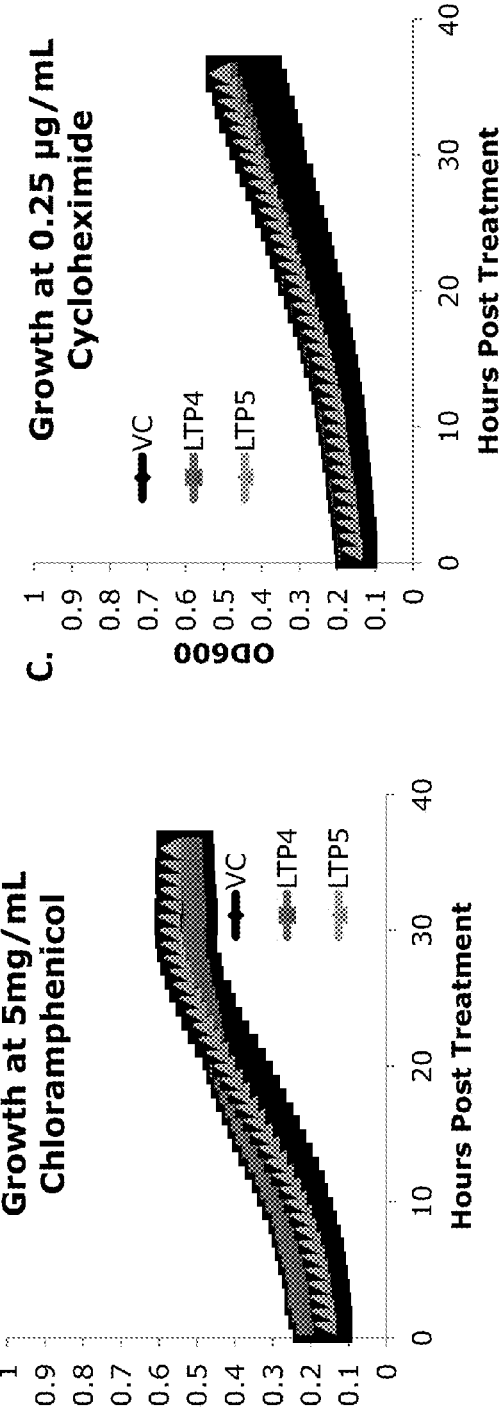

Figure 16.
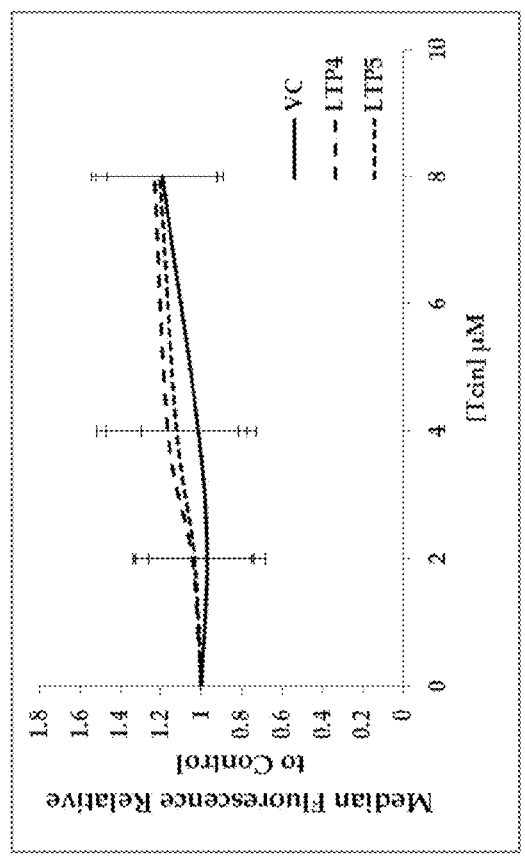
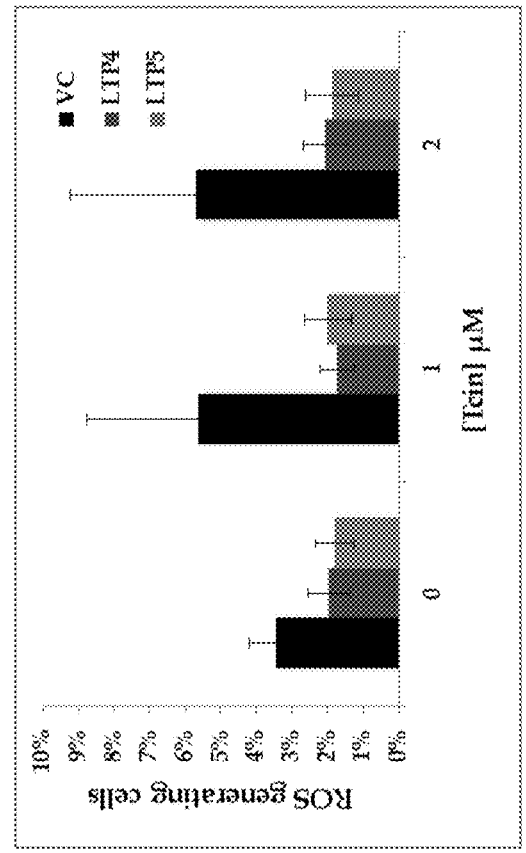

PLANT GENES THAT CONFER RESISTANCE TO TRICHOTHECENE MYCOTOXINS AND FUSARIUM HEAD BLIGHT

This application claims priority to U.S. Provisional Application No. 61/566,095 filed Dec. 2, 2011, the entire contents being incorporated herein by reference as though set forth in full.

The United States government has rights in this invention which was made with funds from the United States Department of Agriculture, ARS Agreement ID: 59-0206-1-121.

FIELD OF THE INVENTION

This invention relates to the fields of molecular biology and transgenic plants. More specifically, the invention provides materials and methods useful for increasing disease resistance in plants.

BACKGROUND OF THE INVENTION

Numerous publications and patent documents, including both published applications and issued patents, are cited throughout the specification in order to describe the state of the art to which this invention pertains. Each of these citations is incorporated herein by reference as though set forth in full.

*Fusarium* Head Blight (FHB) caused mainly by *Fusarium graminearum*, results in yield reductions and in the contamination of cereals with trichothecene mycotoxins, including deoxynivalenol (DON), diacetoxyscirpenol (DAS), T-2 toxin, and trichothecin (T-cin), among others. There is no effective resistance available and the disease pressure and the toxin levels have increased in the last couple of years due to changes in the climate. Using trichodermin as a model compound, trichothecenes were shown to inhibit protein synthesis by targeting the peptidyltransferase center of eukaryotic ribosomes and the gene responsible for the increased trichodermin resistance (TCM1) was shown to encode ribosomal protein L3 (RPL3) in yeast. Trichothecenes have been reported to have diverse roles in the cell that are not limited to the inhibition of protein synthesis. These include single stranded breaks in DNA, inhibition of mitochondrial electron transport and chloroplast activity, membrane damage and inhibition of the cell cycle. There is evidence that DON acts as a virulence factor during *Fusarium* infection. However, the molecular mechanisms that control mycotoxin sensitivity in wheat or barley are not well understood and the genes targeted by DON other than ribosomal protein L3 have not been identified.

SUMMARY OF THE INVENTION

A first aspect of the present invention is directed to a method of identifying genes in plants that effect resistance to fungal mycotoxins, comprising: a) harvesting seed from transgenic plants transformed via *Agrobacterium* with an activation-tagged vector containing an activation tag comprising T-DNA and a promoter functional in the plant (e.g., the CaMV 35s promoter, ubiquitin promoter, etc.); b) cultivating the harvested seed on germination media containing a germination-inhibitory amount of the fungal mycotoxin; c) transferring plants that germinate from the seed and set root in the media, to a growth media and optionally, then to soil; d) isolating DNA from the plants of c); and e) identifying the genomic location of the insertion of the activation tag, and the native structural gene or genes whose expression is altered by the activation tag.

A second aspect of the present invention is directed to a transgenic plant which exhibits increased resistance to a disease caused by a mycotoxin-producing fungus, wherein the plant contains exogenous nucleic acid comprising at least one of the following: a) a first exogenous nucleic acid containing a promoter functional in the plant operably linked to *Arabidopsis* At5G55450 (SEQ ID NO: 1, also referred to as LTP4 or LTP4)) or an ortholog thereof; b) a second exogenous nucleic acid that contains a promoter functional in the plant operably linked to *Arabidopsis* At5G55460 (SEQ ID NO: 2, also referred to herein as LTP5 or LTP5) or an ortholog thereof; and c) an RNAi molecule that hybridizes with *Arabidopsis* At5601620 (SEQ ID NO: 3) or an ortholog thereof. Such plants may optionally include a nucleic acid encoding LTP3 operably linked to a promoter functional in the target plant, e.g., wheat. The nucleic acid constructs, vectors containing them, methods of making the transgenic plants, and transgenic seed obtained from the transgenic seed are also provided.

Other aspects of the present invention are directed to an isolated or purified DNA molecule comprising a non-native promoter functional in the plant operably linked to *Arabidopsis* At5G55450 (LTP4; hereinafter LTP4) or an ortholog thereof, and an isolated or purified DNA molecule comprising a non-native promoter functional in the plant operably linked to *Arabidopsis* At5G55460 (LTP5, herein after LTP5) or an ortholog thereof. The promoter is non-native and drives over-expression of the LTP4, and/or LTP5 or ortholog thereof when transformed in a plant, as compared to native expression levels of these genes. In some embodiments, the non-native promoter is a CaMV35S promoter.

BRIEF DESCRIPTION OF THE DRAWINGS

FIG. 1. Activation-tagged loci AtTRRF 1 identified using TAIL PCR analysis and mapped using T-DNA Express (http://signal.salk.edu/cgi-bin/tdnaexpress). RT-qPCR analysis of neighboring genes revealed upregulation of two neighboring lipid transport genes.

FIG. 2. Western Analysis—*Arabidopsis* total protein samples were separated in a 12% SDS-polyacrylamide gel and the blot was probed with monoclonal anti-His (1:500) followed by anti-mouse (1:5000) IgG (H&L) conjugated with horseradish peroxidase. The membrane was developed with chemiluminescence substrate (Immun-Star HRP Peroxide Buffer/Immun-Star HRP Luminol Enhancer, Bio-Rad), and chemiluminescent signals were captured using the ChemiDoc MP imaging System (Bio-Rad). Below, loading control—Ponceau S Stain (~50 kD band shown). Extra-stripped blot and reprobed with polyclonal antibody raised against mitochondrial serine O-acetyltransferase (SAT1).

FIG. 12. Growth of BY4743 overexpressing LTP4, and LTP5 against inhibitors of translation and yeast growth BY4743 cells overexpressing HA-tagged LTP4 and LTP5 were treated with cycloheximide (A), anisomycin (B), and chloramphenicol (C). OD600 readings were recorded at every 30 min. with continuous shaking at 30° C. in a BioTek (Synergy) plate reader.

FIG. 16. Mitochondrial membrane potential ($\psi$mito) and ROS generation in yeast cells overexpressing LTP4 & LTP5: BY4743 overexpressing LTP4 and LTP5 were treated with increasing concentrations of Tcin for 20 min. (A) Equal OD600 of cells were stained with MitoTracker Red for 30 min. For median fluorescence unit for each treatment was normalized to that of the untreated control. (B) 0.1 OD600 cells were prestained with DCFH-DA for 1.5 h prior to a 20 min. treatment with Tcin. 15000 events were detected using the FL1 (ROS) and FL3 ($\psi$mito) channel and gated as described in Materials and Methods. Error bars indicate S.E. where n=3 independent replicates.

DETAILED DESCRIPTION OF THE INVENTION

Figure 3:
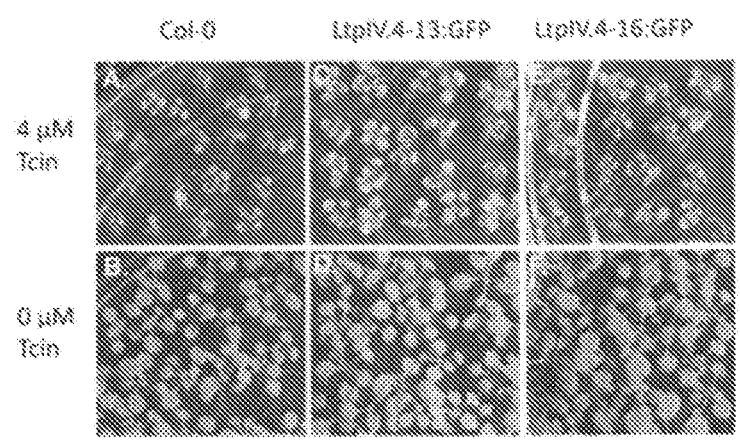
FIG. 3. Germinated Col-0, LTP4-13, LTP4-16 on MS-agar without Tcin. At 14 DPG, seedlings transferred to 4 µM Tcin and allowed to grow for 14 days, plates photographed, and root formation percentage determined.

Trichothecene mycotoxins are potent virulence factors produced by *Fusarium graminearum* during wheat and barley infection leading to the development of the *Fusarium* Head Blight (FHB). This class of mycotoxins inhibits cytosolic and mitochondrial protein synthesis in addition to having other cytotoxic effects. A genetic screen in *Arabidopsis* was undertaken to identify genes that provide resistance to trichothecenes. Approximately 250,000 activation tagged M2 generation *Arabidopsis* seeds were screened for resistance to trichothecin (Tcin), a type B trichothecene, and several lines from this population were identified that showed resistance. These plants were able to form roots on 4 µM Tcin, a concentration which severely restricts root initiation and elongation of the Col-0 wild type following germination. Characterization of one of these resistant lines using RT-qPCR identified an activation genotype, termed *Arabidopsis thaliana* resistant root formation1 or AtTRRF1. In AtTRRF1, two closely linked novel non-specific lipid transfer protein (nsLTP) genes, LTP4 (LTP4; SEQ ID NO: 1) and LTP5, (LTP5; SEQ ID NO: 2) were found to be overexpressed compared to the wild-type control. Both proteins are classified as type IV nsLTPs, a largely uncharacterized class of nsLTPs with limited structural and functional information. Overexpression of both LTP4 and LTP5 independently in *Arabidopsis* confirmed resistance to trichothecin based on differences in the ability to form roots when grown on solid media containing 4 µM Tcin. Overexpression of LTP4 in *Arabidopsis* induced a high level (72.7±10.5) of tolerance, as measured by the percentage seedlings that develop roots when grown on media containing 4 µM Tcin, as compared with control plants (5.6±2.7). Overexpression of LTP5 induced a moderate level (58.6±11.0) of tolerance. Expression of LTP4: GFP and LTP5: GFP was examined by transient expression in tobacco leaves and in the transgenic *Arabidopsis* lines by confocal microscopy. The tagged LTP4 and LTP5 proteins, both containing signal peptides predicted to direct the protein to the apoplast, were found to both localize near the cell wall based on confocal imaging. In addition, coexpression analysis using an ER-mCherry marker in tobacco indicates that LTP4 may also localize to the ER.

In additional experiments, the role of *A. thaliana* derived LTP4 and LTP5 in trichothecene toxicity was investigated. We used the yeast model to show that, similar to their response in *A. thaliana*, overexpression of these two type IV nsLTPs conferred resistance to cells grown against lethal doses of Tcin. Not only was this response unique to these two nsLTPs, this was not seen against other inhibitors of yeast growth. Our results also suggest that mitochondria are likely to play a critical role in nsLTP-mediated resistance to trichothecenes. Yeast cells overexpressing LTP4 and LTP5, in the presence of Tcin, showed little or no inhibition of mitochondrial translation, unlike cytosolic translation which was significantly inhibited. We also showed that reactive oxygen species (ROS) generation, an early time point event during trichothecene toxicity, is alleviated in yeast overexpressing LTP4 and LTP5. Our study, therefore, demonstrates that expression of type IV LTPs confer resistance to trichothecene mycotoxins in yeast and provide insight into the mechanism by which this resistance is attained and the likely role of mitochondria in it.

I. Definitions

The phrases "LTP4 function" or "LTP5 function" is used herein to refer to any activity conferred by the proteins encoded by these genes, including without limitation expression levels of LTP4/5, LTP4/5 enzymatic activity, LTP4/5 protein localization and/or modulation of disease resistance, particularly resistance to fungus infection or toxin exposure.

A "LTP4 homolog" or "LTP5" homolog is any protein or DNA encoding the same which has similar structural properties (such as sequence identity and folding) to the LTPs described herein.

LTP3 function is used herein to refer to any activity conferred by the protein encoded by this gene, including without limitation, LTP3 function, enzymatic activity, protein localization and or modulation of disease resistance.

Orthologs are defined as genes that have diverged after a speciation event. Methods of identifying the orthologs in other plant species are known in the art. Normally, orthologs in different species retain the same function, which in the context of the present invention, is imparting to a transgenic plant increased resistance to at least one fungal mycotoxin (as described below), due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al., 1994, Nucleic Acids Res 22:46734680) may be used to highlight conserved regions and/or residues of orthologous proteins (which may or may not have the same amino acid sequence as the protein encoded by the gene) and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art.

As a result of expression of SEQ ID NO: 1 or SEQ ID NO: 2 in targeted plant species, or an ortholog thereof, or reduced or lack of expression of a native structural gene orthologous to At5G01620 (SEQ ID NO: 3), the transgenic plants of the invention display increased resistance to one or more mycotoxins. Mycotoxins include fumonisin, aflatoxin, ocratoxin, cercosporin, *alternaria* toxins, HC toxin and trichothecenes. Trichothecenes are a class of toxic, sesquiterpenoid secondary metabolites that are produced mainly by plant pathogenic fungi (Fernandez-Lobato et al, Biochem. J. 257:709-713 (1990).

Trichothecenes include trichodermin, dexoynivalenol (DON), diacetoxyscirpenol (DAS), zearalenone, nivalenol, 3-acetyldeoxynivalenol, 15-acetyldeoxynivalenol, fusarenon-X, T-2 toxin and trichotecin (T-cin). *Fusarium graminearum* and *F. culmorum* produce DON, which contaminates a substantial portion of agricultural crops such as wheat, barley, oats, and maize.

Correspondingly, the transgenic plants of the present invention exhibit increased resistance to one or more diseases caused by plant fungi that produce the mycotoxins, including those caused by *Fusarium* (causing root rot of bean, dry rot of potatoes, head blight (scab) in wheat), *Pythium* (one of the causes of seed rot, seedling damping off and root rot), *Phytophthora* (the cause of late blight of potato and of root rots, and blights of many other plants), *Bremia, Peronospora, Plasmopara, Pseudoperonospora* and *Sclerospora* (causing downy mildews), *Erysiphe graminis* (causing powdery mildew of cereals and grasses), *Verticillium* (causing vascular wilts of vegetables, flowers, crop plants and trees), *Rhizoctonia* (causing damping off disease of many plants and brown patch disease of turfgrasses), *Cochliobolus* (causing root and foot rot, and also blight of cereals and grasses), *Giberella* (causing seedling blight and foot or stalk rot of corn and small grains), *Gaeumannomyces* (causing the take-all and whiteheads disease of cereals), *Schlerotinia* (causing crown rots and blights of flowers and vegetables and dollar spot disease of turfgrasses), *Puccinia* (causing the stem rust of wheat and other small grains), *Ustilago* (causing corn smut), *Magnaporthae* (causing summer patch of turfgrasses), and *Schlerotium* (causing southern blight of turfgrasses). Other important fungal diseases include those caused by *Cercospora, Septoria, Mycosphoerella, Glomerella, Colletotrichum, Helminthosporium, Alterneria, Botrytis, Cladosporium* and *Aspergillus*.

The transgenic plants include higher plants including monocots (e.g., cereal crops) and dicots. Specific examples include maize, tomato, turfgrass, asparagus, papaya, sunflower, corn, rye, beans, ginger, lotus, bamboo, potato, rice, peanut, barley, malt, wheat, alfalfa, soybean, oat, eggplant, squash, onion, broccoli, sugarcane, sugar beet, beets, apples, oranges, grapefruit, pear, plum, peach, pineapple, grape, rose, carnation, daisy, tulip, Douglas fir, cedar, white pine, scotch pine, spruce, peas, cotton, flax, canola, ornamentals and coffee.

The transgenic plants may be produced in accordance with standard transformation techniques for the plant type of interest. See U.S. Pat. No. 5,675,322, Horsch et al, Science 227:1229-1231 (1985); and Hartman et al., Bio/technology 72:919-923 (1994).

The invention also includes plant parts (such as leaves, stems, and roots) which display altered expression of one or more genes as described herein resulting in increased resistance to fungal disease or mycotoxin. Also included are protoplasts which include the exogenous nucleic acids as described herein. Further provided are non-naturally occurring or transgenic seed produced by the transgenic plants described herein.

The invention is also directed to methods of making a transgenic plant which display increased resistance to a fungal disease or mycotoxin. In certain embodiments, the transgenic plant has a genome which contains an exogenous nucleic acid comprising a transgene. The transgene may encode a protein which confers resistance to a fungal disease or mycotoxin, or it may encode a protein which interferes with the expression of a gene which confers sensitivity to a fungal disease or mycotoxin.

The method of making a transgenic plant may comprise transforming a protoplast from a cell of a plant. The protoplast may be transformed with the exogenous nucleic acid. The transgenic plant may then be generated from the transformed protoplast and resulting callus. Alternatively, the method comprises introducing the exogenous nucleic acid or genome alteration into tissue of a plant to produce transformed plant tissue, and regenerating the transgenic plant from the transformed plant tissue.

The term "pathogen-inoculated" refers to the inoculation of a plant with a pathogen.

The phrase "disease defense response" refers to a change in metabolism, biosynthetic activity or gene expression that enhances a plant's ability to suppress the replication and spread of a microbial pathogen (i.e., to resist the microbial pathogen). Examples of plant disease defense responses include, but are not limited to, production of low molecular weight compounds with antimicrobial activity (referred to as phytoalexins) and induction of expression of defense (or defense-related) genes, whose products include, for example, peroxidases, cell wall proteins, proteinase inhibitors, hydrolytic enzymes, pathogenesis-related (PR) proteins and phytoalexin biosynthetic enzymes, such as phenylalanine ammonia lyase and chalcone synthase (Dempsey and Klessig, 1995; Dempsey et al., 1999). Such defense responses appear to be induced in plants by several signal transduction pathways involving secondary defense signaling molecules produced in plants.

The terms "defense-related genes" and "defense-related proteins" refer to genes or their encoded proteins whose expression or synthesis is associated with or induced after infection with a pathogen to which the plant is usually resistant.

A "transgenic plant" refers to a plant whose genome has been altered by the introduction of at least one heterologous nucleic acid molecule.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

T-DNA mutagenesis relies on gene inactivation to generate mutant phenotypes. One drawback from screening T-DNA mutants is the problem of gene redundancy. Genetic redundancy can prevent the identification of some genes (ex. members of gene families) by loss-of-function approaches. Accordingly, in order to facilitate identification of resistance genes, the present invention employs an alternative mutagenesis strategy known as activation tagging, which is a technique to analyze unknown gene function, which has been developed for *Arabidopsis thaliana*, and makes it possible to obtain gain-of-function mutants. T-DNA tagging vectors used in activation tagging have enhancers derived from cauliflower mosaic virus (CaMV) 35S promoter. The technique is described in Hayashi, H. et al., Science, 258, 1350-1353, 1992). (See, also, Weigel et al., 2000.) T-DNA contains the CaMV 35S enhancers tandem arranged at a site proximal to the right border. The *Agrobacterium*-mediated introduction of this T-DNA into the plant genome activates and overexpresses genes near the insertion site by the action of the enhancers, with the result that a change occurs in the phenotype of the plant body. For example, a gene involved in hormone signaling (Kakimoto, T. et al., Science, 274, 982-985, 1996) and a gene involved in early flowering phenotypes (Kardailsky, I. et al., Science, 286, 1962-1965, 1999) have previously been reported to be isolated from *Arabidopsis thaliana* by utilizing activation tagging.

Activation tagging has such advantages that: (i) all activation-tagged mutants are dominant and therefore permit the screening of phenotypes in the T1 generation; (ii) mutations in redundantly acting genes can be expected to produce phenotypes; and (iii) there is a high possibility of linking activated genes with dominant mutant phenotypes; and (iv) due to the T-DNA based mutagenesis, recovery of the insertion site is relatively straightforward and can be accomplished by plasmid rescue or TAIL-PCR (see, Singer and Burke, 2003).

The phrase "Ac/Ds transposable element system" refers to a method of mutagenesis employing a transposon which jumps or inserts into a gene of interest (e.g., LTP) and produces a mutation. The presence of the transposon provides a straightforward means of identifying the mutant allele, relative to chemical mutagenesis methods.

"Ac (activator)" is a transposase which enables a transposon to "jump" into different regions in a targeted plant genome.

"Ds (dissociator)" refers to a transposon which upon transposase action inserts and thereby "marks" chromosomal regions where chromosome breakage occurs (e.g., to alter LTP gene expression in a targeted plant).

The terms "percent similarity", "percent identity" and "percent homology" when referring to a particular sequence are used as set forth in the University of Wisconsin GCG software program.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90 95% by weight of the given compound. Purity is measured by methods appropriate for the given compound (e.g. chromatographic methods, agarose or polyacrylamide gel electrophoresis, HPLC analysis, and the like).

A "replicon" is any genetic element, for example, a plasmid, cosmid, bacmid, phage or virus, that is capable of replication largely under its own control. A replicon may be either RNA or DNA and may be single or double stranded.

A "vector" is any vehicle to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15 25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically. The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "promoter region" refers to the 5' regulatory regions of a gene (e.g., CaMV 35S promoters and/or tetracycline repressor/operator gene promoters).

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic delivery, and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "DNA construct" refers to a genetic sequence used to transform plants and generate progeny transgenic plants. These constructs may be administered to plants in a viral or plasmid vector. Other methods of delivery such as *Agrobacterium* T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

The phrase "double-stranded RNA mediated gene silencing" refers to a process whereby target gene expression is suppressed in a plant cell via the introduction of nucleic acid constructs encoding molecules which form double-stranded RNA structures with target gene encoding mRNA which are then degraded.

The term "co-suppression" refers to a process whereby expression of a gene, which has been transformed into a cell or plant (transgene), causes silencing of the expression of endogenous genes that share sequence identity with the transgene. Silencing of the transgene also occurs.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

"Mature protein" or "mature polypeptide" shall mean a polypeptide possessing the sequence of the polypeptide after any processing events that normally occur to the polypeptide during the course of its genesis, such as proteolytic processing from a polyprotein precursor.

A low molecular weight "peptide analog" shall mean a natural or mutant (mutated) analog of a protein, comprising a linear or discontinuous series of fragments of that protein and which may have one or more amino acids replaced with other amino acids and which has altered, enhanced or diminished biological activity when compared with the parent or nonmutated protein.

The present invention also includes active portions, fragments, derivatives and functional or non-functional mimetics of LTP-related polypeptides, or proteins of the invention. An "active portion" of such a polypeptide means a peptide that is less than the full length polypeptide, but which retains measurable biological activity.

A "fragment" or "portion" of an LTP-related polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the LTP-related polypeptide sequence, antigenic determinants, or epitopes are useful for eliciting immune responses to a portion of the LTP-related protein amino acid sequence for the effective production of immunospecific anti-LTP antibodies.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "clone" or "clonal cell population" is a population of cells derived from a single cell or common ancestor by mitosis.

A "cell line" is a clone of a primary cell or cell population that is capable of stable growth in vitro for many generations.

II. Generation of Transgenic Crops with Enhanced Pathogen Resistance by Modulation of Expression of LTP Genes The information provided herein enables the production of crops which exhibit enhanced resistance to plant pathogens. In one approach, transgenic plants, which include, without limitation, barley, wheat, corn, and other crops) will be constructed using vectors encoding the LTP genes described herein. Overexpression of the LTP gene(s) alone or in combination, is induced in a target population of plant cells to increase disease resistance in plants. This elevated expression leads to overproduction of the encoded protein, (e.g., LTP3, LTP4 or LTP5) and serves to increase resistance in certain plant species. Overproduction of LTP(s) in transgenic plant cells may be assessed at the mRNA or protein level using standard technique known in the art such as RT-PCR. Alternatively, overexpression of LTPs by this method may facilitate the isolation and characterization of other components involved in the protein-protein complex formation that occurs during the initiation of the disease resistance response pathway in plants. Inasmuch as the sequence encoding LTP is known for a variety of plant species, overexpression of the LTP encoding nucleic acid is readily achievable in targeted plants species using strong constitutive promoters such as CaMV35S and the like. Alternatively, in cases where inducible expression is preferred, the inducible PR-1 promoter, for example, can be employed. The skilled person in this art area is aware of the many plant vectors and plant gene expression control sequences that are suitable for expression a heterologous gene of interest in a particular plant species.

Transformation techniques for dicotyledons are well known in the art and include *Agrobacterium*-based techniques and techniques which do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3:2717-2722 (1984), Potrykis et al., Mol. Gen. Genet. 199:169-177 (1985), Reich et al., Biotechnology 4:1001-1004 (1986), and Klein et al., Nature 327:70-73 (1987). In each case the transformed cells are regenerated to whole plants using standard techniques.

*Agrobacterium*-mediated transformation is a preferred technique for transformation of dicotyledons because of its high efficiency of transformation and its broad utility with many different species. The many crop species which are routinely transformable by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (Brassica), U.S. Pat. No. 4,795,855 (poplar)). *Agrobacterium* transformation typically involves the transfer of the binary vector carrying the foreign DNA of interest (e.g., pCIB200 or pCIB2001) to an appropriate *Agrobacterium* strain which may depend on the complement of vir genes carried by the host *Agrobacterium* strain either on a co-resident plasmid or chromosomally (e.g., strain CIB542 for pCIB200 (Uknes et al. Plant Cell 5:159-169 (1993)). The transfer of the recombinant binary vector, to *Agrobacterium* is accomplished by a triparental mating procedure using *E. coli* carrying the recombinant binary vector, a helper *E. coli* strain which carries a plasmid such as pRK2013 which is able to mobilize the recombinant binary vector to the target *Agrobacterium* strain. Alternatively, the recombinant binary vector can be transferred to *Agrobacterium* by DNA transformation (H[omicron]fgen & Willmitzer, Nucl. Acids Res. 16:9877 (1988)).

Transformation of the target plant species by recombinant *Agrobacterium* usually involves co-cultivation of the *Agrobacterium* with explants from the plant and follows protocols known in the art. Transformed tissue is regenerated on selectable medium carrying an antibiotic or herbicide resistance marker present between the binary plasmid T-DNA borders.

Preferred transformation techniques for monocots include direct gene transfer into protoplasts using PEG or electroporation techniques and particle bombardment into callus tissue. Transformation can be undertaken with a single DNA species or multiple DNA species (i.e., co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al., Biotechnology 4:1093-1096 (1986)).

Published Patent Applications EP 0292435, EP 0392225 and WO 93/07278 describe techniques for the preparation of callus and protoplasts of maize, transformation of protoplasts using PEG or electroporation, and the regeneration of maize plants from transformed protoplasts. Gordeon-Kamm et al., Plant Cell 2:603-618 (1990), and Fromm et al., Biotechnology 11:194-200 (1993), describe techniques for the transformation of elite inbred lines of maize by particle bombardment.

Transformation of rice can also be undertaken by direct gene transfer techniques utilizing protoplasts or particle bombardment. Protoplast-mediated transformation has been described for Japonica-types and Indica-types (Zhange et al., Plant Cell Rep. 7:739-384 (1988); Shimamoto et al. Nature 338:274-277 (1989); Datta et al. Biotechnology 8:736-740 (1990)). Both types are also routinely transformable using particle bombardment (Christou et al. Biotechnology 9:957-962 (1991)).

Patent Application EP 0 332 581 described techniques for the generation, transformation and regeneration of Pooideae protoplasts. Furthermore wheat transformation has been described by Vasil et al., Biotechnology 10:667-674 (1992), using particle bombardment into cells of type C long-term regenerable callus, and also by Vasil et al., Biotechnology 11:1553-1558 (1993), and Weeks et al., Plant Physiol. 102: 1077-1084 (1993), using particle bombardment of immature embryos and immature embryo-derived callus.

Transformation of monocot cells such as *Zea mays* can be achieved by bringing the monocot cells into contact with a multiplicity of needle-like bodies on which these cells may be impaled, causing a rupture in the cell wall thereby allowing entry of transforming DNA into the cells. See U.S. Pat. No. 5,302,523. Transformation techniques applicable to both monocots and dicots are also disclosed in the following U.S. Pat. No. 5,240,855 (particle gun); U.S. Pat. No. 5,204,253 (cold gas shock accelerated microprojectiles); U.S. Pat. No. 5,179,022 (biolistic apparatus); U.S. Pat. Nos. 4,743,548 and 5,114,854 (microinjection); and U.S. Pat. Nos. 5,149,655 5,120,657 (accelerated particle mediated transformation); U.S. Pat. No. 5,066,587 (gas driven microprojectile accelerator); U.S. Pat. No. 5,015,580 (particle-mediated transformation of soy bean plants); U.S. Pat. No. 5,013,660 (laser beam-mediated transformation); and U.S. Pat. Nos. 4,849,355 and 4,663,292.

The transgenic plant cells or plant tissue are then grown into full plants in accordance with standard techniques. Transgenic seed can be obtained from transgenic flowering plants in accordance with standard techniques. Likewise, non-flowering plants such as potato and sugar beets can be propagated by a variety of known procedures. See e.g., Newell et al, *Plant Cell Rep.* 10:30-34 (1991) (disclosing potato transformation by stem culture).

The invention also includes transgenic plants and plant parts produced by any of the above techniques, non-naturally occurring seed obtained from such plants, as well as transformed protoplasts produced by the methods described above.

In embodiments where the gene, e.g., At5G01620 or an ortholog thereof, confers sensitivity to fungal disease or mycotoxin, transgenic plants may be prepared using standard techniques which result in downregulated expression or complete obliteration of gene expression. The downregulation may be the result of introduction of sequences which interfere with gene expression, such as antisense constructs, sense constructs, RNA silencing constructs, or RNA interference; or it may be the result of genomic disruptions of the sensitivity gene itself through the use of, for example, transposons, tilling, homologous recombination, or nonsense mutations.'

Use of antisense nucleic acids is well known in the art. The antisense nucleic acid can be RNA, DNA, a PNA or any other appropriate molecule. An antisense nucleic acid can be produced, e.g., for a sensitivity gene by a number of well-established techniques (e.g., chemical synthesis of an antisense RNA or oligonucleotide (optionally including modified nucleotides and/or linkages that increase resistance to degradation or improve cellular uptake) or in vitro transcription). Antisense nucleic acids and their use are described, e.g., in U.S. Pat. Nos. 6,242,258; 6,500,615; 6,498,035; 6,395,544; and 5,563,050.

Another method to inhibit sensitivity gene expression is by sense suppression. Introduction of expression cassettes in which a nucleic acid is configured in the sense orientation with respect to the promoter has been shown to be an effective means by which to block the transcription of a desired target gene. See, e.g., Napoli et al. (1990), The Plant Cell 2:279-289, and U.S. Pat. Nos. 5,034,323, 5,231,020, and 5,283,184.

An RNAi approach may also be used to silence orthologs of the *Arabidopsis* At5G01620 trichome birefringence gene. For example, gene in wheat or barley, 500-1000 bp sequence corresponding to the most highly conserved region of the At5G01620 will be cloned in both orientations into the *Agrobacterium* binary vector pBRACT207 (3) (http://www.bract.org/constructsavailable/pBractVectors/Constructs/constructs.html), to generate a hairpin for gene silencing in barley. This plasmid may be used for wheat and barley transformation using either the particle gun or the *Arabidopsis* mediated transformation. For *Arabidopsis* mediated transformation of barley, the plasmid may be introduced into *Agrobacterium* strain AGL1 (3, 11). Golden Promise and Conlon embryos may be isolated from barley (5) and two-week old callus tissue may be inoculated with AGL1 containing the binary vector (3). Hygromycin may be used to select the barley cells containing the inserted gene. DNA may be isolated from leaf tissue (8) and analyzed by polymerase chain reaction (PCR) and Southern hybridization to test for the presence of the inserted gene. Expression level of the genes may be analyzed by quantitative reverse transcriptase PCR (qRT-PCR) in homozygous progeny. Susceptibility of the seedlings to Tcin and DIN may be evaluated by seed germination assays on media containing the toxins. The references provided below set forth several of these techniques. (Bartlett, J. G., S. C. Alves, M. Smedley, J. W. Snape, and W. A. Harwood. 2008. High-throughput *Agrobacterium*-mediated barley transformation. Plant Methods 4:22; Dahleen, L. S., and P. Bregitzer. 2002. An improved media system for high regeneration rates from barley immature embryo-derived callus cultures of commercial cultivars. Crop Sci 42:934-38; Faris, J. D., K. M. Haen, and B. S. Gill. 2000. Saturation mapping of a gene-rich recombination hot spot region in wheat. Genetics 154:823-35).

The aforementioned approaches are suitable for modulating expression of genes of interest in targeted plants thereby enhancing pathogen resistance in crops, such as barley, tomato and potato (soybean).

SEQUENCE INFORMATION FOR GENES ASSOCIATED WITH ALTERED RESISTANCE TO Tcin

LTP4 (*Arabidopsis*) nsLTp
Gene Model: AT5G55450.1
CDS sequence:

(SEQ ID NO: 1)
ATGGGTAAGGACAACACCAGAATCCTCATGCAATTTTCAGCTCTCGCGATGGTTTTAACAGCTGC

AATAATGGTGAAAGAAGCTACAAGCATTCCCGTTTGCAACATTGACACAAACGACTTGGCGAAA

TGCCGTCCAGCCGTCACTGGAAACAACCCTCCACCACCGGGACCGGACTGCTGCGCAGTGGCCA

GAGTTGCTAATCTACAATGCCTCTGCCCGTACAAGCCTTATCTCCCCACTGTCGGGATAGACCCA

TCTAGAGTCAGGCCTCTTCTTGCCAATTGTGGTGTAAACAGTCCTTCCTGTTTCTAA

Protein: AT5G55450.1 UniProtKB (Q9FJ65) GenPept 18423748

(SEQ ID NO: 5)
MGKDNTRILMQFSALAMVLTAAIMVKEATSIPVCNIDTNDLAKCRPAVTGNNPPPPGPDCCAVARVA

NLQCLCPYKPYLPTVGIDPSRVRPLLANCGVNSPSCF

LTP5 (*Arabidopsis*) nsLTP
Gene model: AT5G55460.1
CDS sequence:

(SEQ ID NO: 2)
ATGGATACGAACAATACCAGAACTGTGAAATTTGCAGCTCTTGCAATAGTTTTAGCCGCCTTGGT

GTTGATGGAAGAACCTACGAGCATTACCGCATGTAACATCAACGCAAACCATCTGGAAAAATGT

CGTCCAGCCGTAATTGGAGACAACCCGCCATCTCCAATCAAAGAGTGTTGTGAACTCCTCCAAG

CCGCTAATCTGAAATGCATCTGCAGATTCAAGTCTGTTCTCCCCGTTTTAGCGGTTTACCCATCT

-continued

AAAGTCCAGGCTCTTCTGAGCAAATGTGGCCTGACAACAATCCCTCCTGCTTGCCAAGCTTTGA

GGAACTGA

Protein AT5G55460.1: UniProtKB (Q8GWA4) GenPept 30696602
(SEQ ID NO: 6)
MDTNNTRTVKFAALAIVLAALVLMEEPTSITACNINANHLEKCRPAVIGDNPPSPIKECCELLQAANL

KCICRFKSVLPVLAVYPSKVQALLSKCGLTTIPPACQALRN

AY226580 (Wheat LTP3)
Probable non-specific lipid-transfer protein 3
Full length CDS sequence:
SEQ ID NO: 4
ATGG CTCGTCTCAA CAGCAAGGCT GTGGCGGCCG CCGTGGTCCTGGCGGCGGTG

GTGCTGATGATGGCCGGCAG GGAGGCCTCG GCGGCGCTGT CGTGCGGGCAGGTGGACTCC

AAGCTCGCGC CGTGCGTGGC GTACGTGACG GGGAGGGCGT CCTCGATCAGCAAGGAGTGC

TGCTCCGGCG TGCAGGGGCT GAACGGCCTG GCCCGCAGCA GCCGGACCGCAAGATAGCG

TGCAGGTGCC TCAAGAGCCT CGCCACCAGC ATCAAGTCCA TCAACATGGGCAAGGTCTCC

GGCGTGCCCG GCAAGTGCGG CGTCAGCGTG CCCTTCCCCA TCAGCATGTCCACCAACTGC

AACAATGTCA ACTAG

Gramene-Protein Q84N29
(SEQ ID NO: 8)
MARLNSKAVAAAVVLAAVVLMMAGREASAALSCGQVDSKLAPCVAYVTGRASSISKECCSGVQGLNGL

ARSSPDRKIACRCLKSLATSIKSINMGKVSGVPGKCGVSVPFPISMSTNCNNVN

At5G01620.3 (Arabidopsis)
TBL35, TRICHOME BIREFRINGENCE-LIKE 35
(SEQ ID NO: 3)
ATGTCGCAGAGATGGAGTAGAAAGAAGAGTAGACTTCCATTAGCGGGTCTCCTCTTTATTCTCG

TTGTCACCTTTATGATTCTCTTCAACGAGCGTAGCATTCAGCAGATCCATCACCACGCCGCGAGT

CACACTCAAAATCTCCGAGAACCTTCCACGTTCGATTTCGTCAAGCCTAATGTTCCTCGGATTAA

CTACTTGGGAGCTCATGGATTCTGTTTTGAAAAAAATGCAGAGGTTTTGGATAGATTCAGCAAAT

GCAACTCGACGAAAGAGTACAGTGGGAAGAAAATCGGATGGGTTGACCCGTTTGAAGACCACCC

GGGTCAAGTAACAAAGGAGGAGCAGAAATGTGATGTCTTTTCTGGGAAATGGGTCTTTGATAAT

TCATCATCATACCCTTTACACAAGGAATCTCAGTGTCCTTACATGTCCGACCAGTTGGCTTGTCA

GAAGCATGGTAGGAAGGATTTGGAGTATCAGCATTGGAGATGGCAACCTCATGCCTGCAACTTG

AAGAGATGGAATGCGATAGAAATGTGGGAGAAGCTGAGAGGAAAGAGATTGATGTTTGTTGGA

GACTCGTTAAACAGAGGCCAATGGATTTCAATGGTTTGTCTCTTACAGTCTGTCATTCCACGTGA

CAAGCAGTCTATGTCTCCTAACGCTCACCTCACCATTTTCAGGGCTGAGGACTACAATGCCACAG

TGGAGTTTCTCTGGGCACCGTTGCTCGTGGAGTCGAATTCTGATGACCCTGTTAATCACAGATTG

AGCGAGCGGATTATCCGACCCGATTCTGTTCTTAAACATGCATCAAAGTGGCAACATGCTGATAT

TCTAATCTTCAACACCTACTTATGGTGGAGACAAGACTCTGTCAAGCTCCGATGGAGCAGTGAA

GAAAAAGGGTCATGCGAGGAGGTGAAGAGCGCCGAGGGAATGGAGATGGCAATGGATAGTTGG

GGTGATTGGGTTGCTAACAATGTCGATCCAAACAAAAAGCGAGTTTTCTTCGTTACAATGTCTCC

TACACATCAATGGAGCCGAGAATGGAACCCGGGAAGCGAAGGAAACTGCTACGGGGAGAAGAA

ACCAATAGAGGAAGAGAGTTATTGGGGAAGTGGGTCGGACATTCCGACAATGAGGATGGTGAA

GAGAGTTTTGGAGAGATTGGGACCAAAGGTCTCAGTTATAAACATCACTCAGTTGTCTGAGTAT

CGAAAAGATGGTCATCCATCGGTGTACCGGAAATTCTGGGAACCTCTAAATGAAGACCGGTTGA

-continued

```
AAAACCCGGCATCGTATTCTGACTGTACTCATTGGTGTGTACCTGGAGTTCCTGATGTCTGGAAT

CAATTGCTTTTCCATTTTTTGTGA

Protein: AT5G01620.3
                                                            (SEQ ID NO: 7)
MSQRWSRKKSRLPLAGLLFILVVTFMILFNERSIQQIHHHAASHTQNLREPSTFDFVKPNVPRINYLG

AHGFCFEKNAEVLDRFSKCNSTKEYSGKKIGWVDPFEDHPGQVTKEEQKCDVFSGKWVFDNSSSYP

LHKESQCPYMSDQLACQKHGRKDLEYQHWRWQPHACNLKRWNAIEMWEKLRGKRLMFVGDSLN

RGQWISMVCLLQSVIPRDKQSMSPNAHLTIFRAEDYNATVEFLWAPLLVESNSDDPVNHRLSERIIRP

DSVLKHASKWQHADILIFNTYLWWRQDSVKLRWSSEEKGSCEEVKSAEGMEMAMDSWGDWVANN

VDPNKKRVFFVTMSPTHQWSREWNPGSEGNCYGEKKPIEEESYWGSGSDIPTMRMVKRVLERLGPK

VSVINITQLSEYRKDGHPSVYRKFWEPLNEDRLKNPASYSDCTHWCVPGVPDVWNQLLFHFL
```

III. Methods of Using the Transgenic Yeast of the Invention in Screening Assays to Identify Agents which Modulate LTP or Other Targeted Gene Activity Since the genes identified herein have been associated with the fungal resistance, methods for identifying agents that modulate the activity of the genes and their encoded products should result in the generation of efficacious antifungal agents.

Molecular modeling should facilitate the identification of specific organic molecules with capacity to bind to the active site of the proteins encoded by these nucleic acids based on conformation or key amino acid residues required for function. A combinatorial chemistry approach will be used to identify molecules with greatest activity and then iterations of these molecules will be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd.(Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. See Example II. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered LTP gene. These host cell lines or cells are defective at the polypeptide level. The host cell lines or cells are grown in the presence of drug compound. The lipid transfer in the host cells is measured to determine if the compound is capable of regulating this feature in the defective cells. Host cells contemplated for use in the present invention include but are not limited to yeast cells, fungal cells, insect cells, mammalian cells, and plant cells. The LTP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

Cells and cell lines suitable for studying the effects of the nucleic acids identified herein on fungal resistance nd methods of use thereof for drug discovery are provided. Such cells and cell lines will either already express the gene of interest or be transfected with a nucleic acid(s) described herein and the effects on fungal resistance or other parameters may be determined. Such cells and cell lines will also be contacted with the siRNA molecules provided herein to assess the effects thereof on fungal resistance.

A wide variety of expression vectors are available that can be modified to express the novel DNA or RNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Example II and in Current Protocols in Molecular Biology (1989).

The following examples are provided to illustrate certain embodiments of the invention. They are not intended to limit the invention in any way.

Materials and methods are provided to facilitate the practice of Example I.

Plant Materials

The activation tagged *Arabidopsis thaliana* lines were in the Columbia (Col-0) background, which also represents the wild type used in this study. The activation tagged population was generated by an *Agrobacterium*-based transformation with the pSKI015 plasmid containing the modified T-DNA construct [28] via the floral dip method[39]. The modified T-DNA vector contains the tetramerized cauliflower mosaic virus (CaMV) 35S gene enhancer. For the overexpression work, Col-0 plants were later transformed using the *Agrobacterium*-based floral dip method with vectors containing LTP4 and LTP5

Trichothecin Mycotoxin

Tcin was isolated from *Trichothecium roseum* and prepared as described previously [16].

RNA Extraction and Quantification

Total RNA was extracted using TRIzol reagent (Invitrogen) followed by column purification (RNeasy mini kit; Qiagen). RNA was quantified using the BioTek Synergy4™ Take3™ 2 μL volume (260/280 nM) read. The RNA sample concentration was determined using a BioTek Synergy4™ spectrophotometer with the Take3™ plate and the absorbance at 260/280 nm was obtained. The RNA quality was assessed by running the RNA on a gel and observing intact 18 and 28S rRNA bands without significant smear.

RT-qPCR

Real-time quantitative PCR(RT qPCR) using SYBR Green was used to quantify gene expression of genes neighboring both At5G55440 for AtTRRF1. The Comparative Ct method (ΔΔCt) method was used to quantity gene expression using the Actin8 gene for normalization relative to the Col-0 control.

Thermal Asymmetric Interlaced (TAIL) PCR

The identified activation tagging mutants identified were characterized by (TAIL) PCR[35]. The amplified band of verified activation tagged mutants were sequenced and the genomic location of the inserts was mapped using TDNA express (http://signal.salk.edu/cgi-bin/tdnaexpress).

In Vitro Germination Bioassay

*Arabidopsis* germination media consisted of 2 g Murashige and Skoog (MS) media, 14.6 mg EDTA-Fe and 4.8 g Phytagel (Sigma P-8169), 720 mL DI water and 80 mL tap water. The media was autoclaved and trichothecin was added to the media before pouring the germination/growth plates.

Example I

Activation Tagging in *Arabidopsis* Identifies Two Novel Non-Specific Lipid Transfer Proteins Which Provide Enhanced Resistance to a Trichothecene Mycotoxin In this study we used activation tagging to generate mutants to screen for resistance to trichothecin, a type B trichothecene in the same class as DON. Activation tagging is an insertional mutagenesis strategy, in which a regulatory sequence (enhancer or promoter) is randomly inserted in the genome, such that it can potentially alter the transcriptional pattern of an endogenous gene resulting in a mutant phenotype[27,28]. In activation tagging with *Arabidopsis*, we used a T-DNA vector (pSKI015[28]) which contains four copies of the CaMV35S promoter enhancer sequence laid out in tandem, so dominant gain-of-function mutants could be identified in the screen, in addition to T-DNA knockouts. The advantages of this method are that both overexpression and loss-of-function mutants can be generated in the same population. A further advantage of the T-DNA insertional mutagenesis is that recovery of the insertion site is relatively straightforward either by plasmid rescue or TAIL-PCR [29]. The mutation can be cloned using the insertion sequence as a molecular tag to discover the flanking genomic DNA and thus the location of the insert. Unlike most knockout phenotypes, gain-of-function mutants behave dominantly so they can be identified in the F1 generation. Activation tagging has been used to identify numerous novel genes in *Arabidopsis* such as the floral inducer FT gene [30] and plant pathogen resistance genes [31](see [32] for review). In addition, activation tagging is beginning to be used in crop species such as wheat and barley, using genetically engineered Ds elements containing enhancers or promoters, to identify agronomically significant genes directly[33,34]

Results

Our activation tagging screen of 250,000 M2Arabidopsisplants identified 30 mutants which were able to germinate and grow in the presence of 4 μM Tcin, a concentration that severely limited root growth of the wild type, Col-0. These plants were largely indistinguishable from the untreated wild type plants, expect for one dwarf mutant identified. DNA from one Tcin resistant mutant, AtTRRF1, was isolated and thermal asymmetric interlaced (TAIL) PCR [35] was used to identify the genomic sequences flanking the insertion tag. The nested and degenerate primers used for TAIL PCR are listed in tables 1 and 2, respectively. The T-DNA tag inserted into the last exon of the At5G55440 gene, encoding for a protein of unknown function (DUF295) based on the *Arabidopsis* Information Resource (TAIR) database [36]. To determine how the insert affected gene transcription in this region, RT-qPCR was performed on cDNA isolated from leaf tissue collected from Col-0 and AtTRRF1. Five primer sets designed for At5G55420 (data not shown), At5G55430, At5G55440, At5G55450, and At5G55460 (two upstream, the knockout, and two downstream genes) were used in the triplicate RT-qPCR reactions. Primers for these sequences are listed in table 3. Little or no expression was detected for either the wild type or AtTRRF1 using primers designed to amplify At5G55420, At5G55430 or At5G55440. However, At5G55450 and At5G55460 were found to be induced 12 and 14 fold, respectively, relative to the wild type (FIG. 1) indicating the possibility that overexpression of both or either of these genes gives rise to the resistance phenotype. At5G55450 and At5G55460 represent two novel lipid transfer protein (LTP) genes, previously designated as LTP4 and LTP5 [37]. This pair of genes likely represents a tandem duplication repeat (Blast alignment reveals an E value of $3 \times 10^{-28}$).

TABLE 1

(provided sequences are SEQ ID NOs: 9-11 from top to bottom).

| Nested Primers | Sequence | PCR Stage |
|---|---|---|
| BG646 | Acgctgcggacatctacattttg | TAIL1 |
| BG647 | Cttttcctccatattgaccatc | TAIL2 |
| BG648 | Catactcattgctgatccatgtaga | TAIL3 |

TABLE 2

(provided sequences are SEQ ID NOs: 12-15 from top to bottom).

| Arbitrary degenerate (AD) | Sequence |
|---|---|
| BG649 | NGTCGASWGANAWGAA |
| BG650 | TGWGNAGSANCASAGA |
| BG651 | AGWGNAGWANCAWAGG |
| BG652 | STTGNTASTNCTNTGC |

TABLE 3

Primer sequences, the amplicon length and melting temperature of the primers used for reference genes and a genes of interest. Foward primer sequences are SED ID NOs: 16-22 from top to bottom and reverse primer sequences are SEQ ID NOs: 23-29 from top to bottom.

| Symbol | Forward primer sequence (5'-3') | Tm (° C.) | Reverse primer sequence (5'-3') | Tm (° C.) | Amplicon length (bp) |
|---|---|---|---|---|---|
| ACT8 | ATGAAGATTAAGGTCGTGGCAC | | GTTTTTATCCGAGTTTGAAGAGGC | | |
| AT5G55430 | GTACGTTGCTTTCCCCAAGA | | ACCGCTACATCCTCGACATC | | |
| AT5G55440 | GTGGATTCTCCCTCTGGTGA | 60.05 | CCCATCTTGCCTAAAGACCA | 60.07 | 217 |
| AT5G55450 | TGCAACATTGACACAAACGA | 59.72 | ATGGGTCTATCCCGACAGTG | 59.80 | 160 |
| AT5G55460 | CGCAAACCATCTGGAAAAAT | 59.94 | CAAGCAGGAGGGATTGTTGT | 60.11 | 204 |
| LTP4 | ATGGGTAAGGACAACACCAG | | GAAACAGGAAGGACTGTTTACAC | | |
| LTP5 | ATGGATACGAACAATACCAGAAC | | GTTCCTCAAAGCTTGGCA | | |

Figure 7:
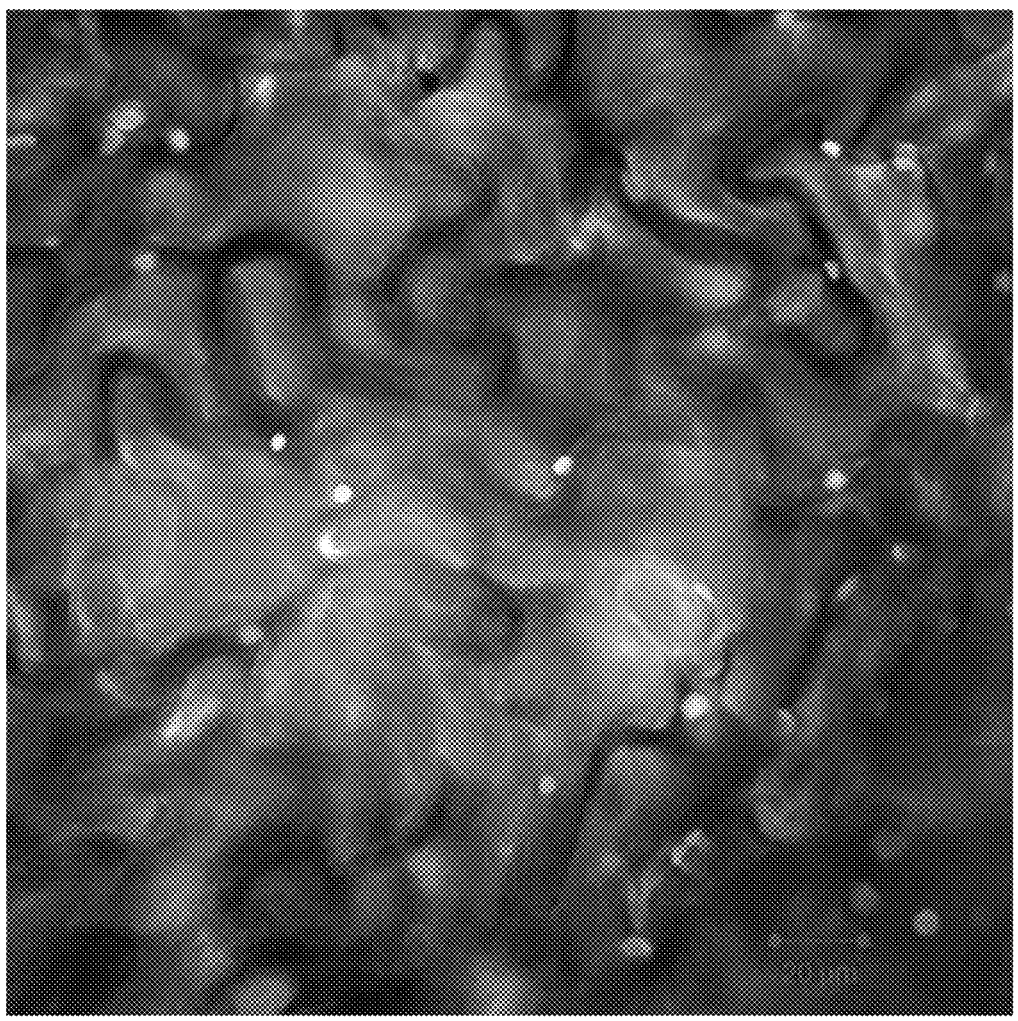
FIG. 7. Confocal images of *Arabidopsis* LTP4 (line 4) leaf tissue.
Figure 8:
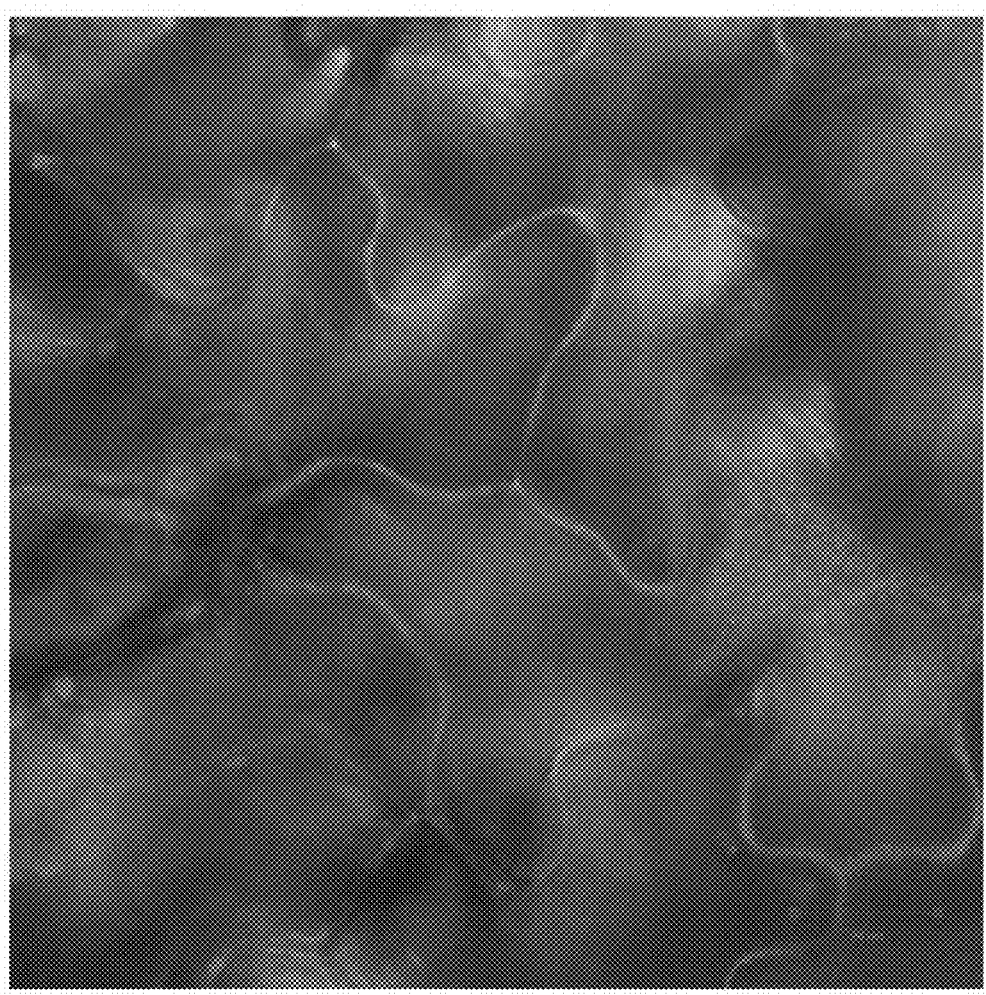
FIG. 8. Confocal image of *Arabidopsis* LTP5::GFP (line 46).

To determine if overexpression of either LTP4 or LTP5 in *Arabidopsis* confers trichothecene resistance, both genes were cloned and expression vectors containing C-terminal fusions with GFP driven by the CaMV35S promoter were independently generated. Both the LTP4 and LTP5 genes without the stop codon were amplified by RT-PCR from RNA isolated from the AtTRRF1 line. The gene was cloned into the entry vector pCR8/GW/TOPO (Invitrogen) by TOPO TA cloning. Sequence analysis confirmed the sequence fidelity of the cloned gene. LTP4 and LTP5 were then subcloned by performing a LR recombination reaction into the binary vector pEarleyGate 103 (35S-Gateway-GFP-His tag-OCS 3') (28). This plasmid was then transformed into *Agrobacterium* (GV3101MP90 strain)(29). Expression of LTP4:GFP and LTP5:GFP was examined independently by transient expression in tobacco leaves by confocal microscopy (FIGS. 7 and 8). Leaf disks were visualized with a Zeiss LSM 710 laser scanning microscope. Both GFP and chlorophyll were excited with a 488-nm argon laser and the fluorescence was detected using 495-570 nm and 650-760 nm bandpass filters, respectively. Image data was collected and analyzed with the Zen 2010 software (Carl Zeis Microimaging, Thornwood, N.Y.). Both the LTP4::GFP and LTP5::GFP fusions were seen to strongly express in the tobacco leaf and GFP signal localized to the extracellular space near the cell wall, which is consistent with the predicted localization information available through the *Arabidopsis* Subcellular Proteomic Database (SUBA)[38]. Following confirmation that the LTP4::GFP and LTP5::GFP constructs expressed in tobacco, Col-0 plants were transformed with these vectors using the floral dip procedure [39] and transgenic lines were identified by plating the seeds on MS media containing Basta (25 μg/mL) to identify Basta resistant seedlings. A number of independent transgenic lines individually expressing LTP4 and LTP5 were developed by growing the Basta resistant seedlings in soil using a growth chamber maintained at 24° C. in a 16/8 h day/night cycle. Resulting seed from each line was tested again on solid MS media containing Basta and 4 μM Tcin. Resulting seedlings that grew with both the Basta and 4 μM Tcin were advanced on soil to generate seed for testing resistance. Six lines for each gene were tested using a germination assay on 4 μM Tcin using Col-0 as the non-transgenic control.

Figure 4:
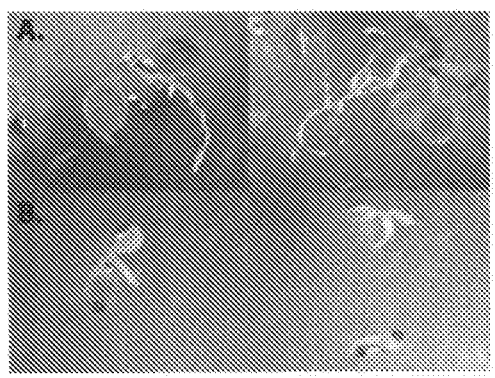
FIG. 4. LTP5 transgenic *Arabidopsis* seedlings (A) and wild type (B) and on 4 µM Tcin for 3 weeks.
Figure 5:
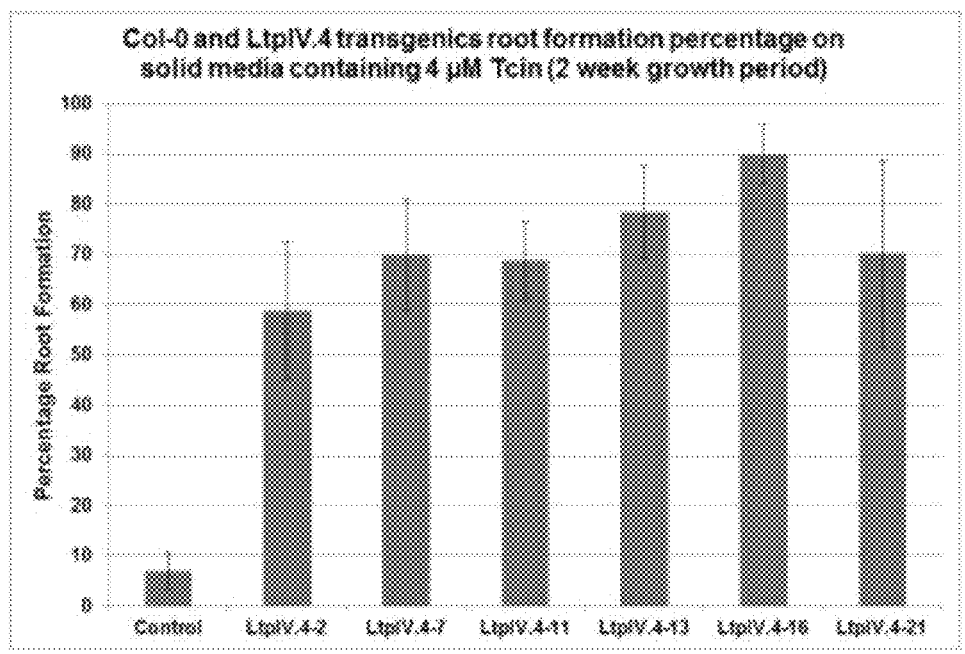
FIG. 5. Root formation percentage of wild type and five LTP4 lines grown 4 µM Tcin. Root formation percentage was determined after 2 weeks of growth.
Figure 6:
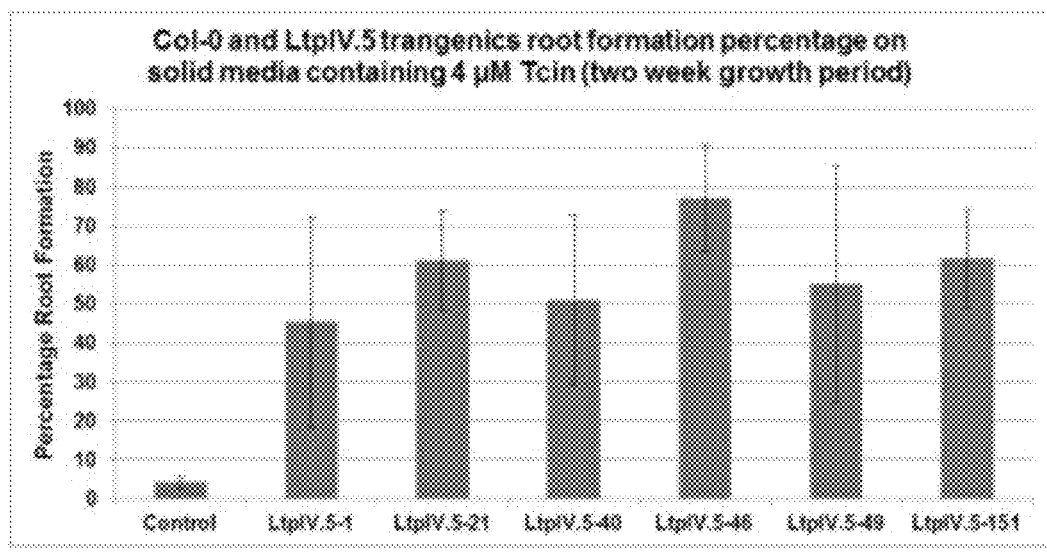
FIG. 6. Root formation percentage of wild type and five LTP5 lines grown in 4 µM Tcin. Root formation percentage was determined after two weeks of growth.

As shown in FIGS. 3 and 4, transgenic lines LTP4-13 and LTP4-16 showed improved root and vegetative growth on media containing 4 micromolar trichothecin. A quantitative assessment of percentage root formation for different LTP4 and LTP5 transgenic lines relative to control is presented in FIGS. 5 and 6, respectively. Root formation percentage was determined after 2 weeks of growth using ~100 seedlings per genotype. As shown in FIG. 5, six different transgenic lines expressing LTP4 showed significantly greater root growth compared to the wild type Col-0 (control). As shown in FIG. 6, six different transgenic lines expressing LTP5 showed significantly better root growth than the wild type Col-0 control. These results demonstrate that expression of LTP4 (LTP4) and LTP5 (LTP5) in transgenic plants confers resistance to trichothecene mycotoxins. Since trichothecene mycotoxins are virulence factors for *Fusarium graminearum*, it is expected that transgenic cereal lines (what, barley oat, maize, etc) expressing these genes will show resistance to *Fusarium* Head Blight.

Another M2 plant identified from the screen was named *Arabidopsis thaliana* resistance formation 5 (AtTRRF5). M3 seed was grown and genotyped to confirm the presence of the activation tag. TDNA Express (signal.salk.edu), an *Arabidopsis* gene mapping tool to identify the genomic location of the TDNA inserts, was used to identify the genomic location of the activation tag for this mutant. The activation tag for AtTRRF5 maps to the second exon of At5G01620, which encodes a member of the TBL (TRICHOME BIREFRINGENCE-LIKE) gene family. TBL proteins involve the synthesis and deposition of secondary wall cellulose (Bischoff et al.).

At5G01620 (SEQ ID NO: 3) belongs to a plant specific poorly described gene family with 46 members in *Arabidopsis*. A null mutation in a related PMR5 gene rendered *Arabidopsis* resistant to powdery mildew (Vogel et al., 2004). Both genes are found on chromosome 5, but are not linked. Since the T-DNA contains enhancer elements near the right border, the enhancer might have caused activation of the nearby genes. CaMV35S enhancers in pSKI015 can work either upstream or downstream of a gene (Nakazawa et al., 2003; Weigel et al., 2000). The ORF downstream of the enhancer encodes an ortholog of human breast cancer susceptibility gene AT5G01630 in AtRRF5 and the two ORFs upstream of the enhancer encode two unknown proteins, AT5G01590 and AT5G01610 in AtRRF5. It has been shown that genes as far away as 12 kb can be induced by the CaMV enhancer elements (Jeong et al., 2006; Qu et al., 2008). PCR primers for the neighboring genes were designed to test for overexpression of the genes which contain the T-DNA insertions, as well as the nearby genes relative to Col-0 using semiquantitative RT-PCR (Pierce et al.).

To determine if resistance is due to loss-of-function mutations in these genes, or to activation of expression of nearby genes, we used quantitative real time PCR (qRT-PCR) to examine the expression of these genes in Col-0 and in the activation tagged line. AtTRRF5 was grown to maturity and seed was collected. RNA was isolated from three M3 plants. In addition, RNA was isolated from Col-0, which represents the wild type background of the activation tagged population. Real-time quantitative PCR(RT qPCR) using SYBR Green was used to quantify gene expression of genes neighboring At5G01620 (Table 4) The Comparative Ct method (ΔΔCt) method was used to quantity gene expression using the Actin 8 gene for normalization relative to the Col-0 control. Expression of the activation tagged gene, AT5G01620 was not detected in AtTRRF5, compared to wild type Col-0. No gene expression changes were noted for the three genes that surround the tagged At5G01620, indicating that the resistant phenotype for AtTRRF5 is likely due to disruption of this gene. These results were confirmed by testing SALK knockouts of At5G01620 and demonstrating that knockout of this gene was responsible for trichothecene resistance.

TABLE 4

| Gene Name | Function | Fold Expression Change |
|---|---|---|
| AT5GO1590 | Unknown | NSD* |
| AT5G1610 | Unknown | NSD |
| AT5GO1620 | Unknown | Knockout relative to control |
| AT5GO1630 | BRAC2V | NSD |

Discussion

An activation tagging strategy using *Arabidopsis* identified two nsLTPs that, upon overexpression, gives enhanced tolerance to the presence of trichothecin, a type-B trichothecene. Trichothecin inhibits both *Arabidopsis* root growth and vegetative development. Tcin is in the same class of trichothecenes as DON and was used in the screen because *Arabidopsis* is more sensitive. In addition, Tcin is produced by *Fusarium graminearum [*40] and likely serves as a virulence factor like DON [19,20].

LTP4 (At5g55450) and LTP5 (At5g55460) functions are predicted but unknown. These genes are the likely result of tandem duplication with LtpIV.3 (At5g55410), LTP4 (At5g55450) and LTP5 (At5g55460) closely linked on chromosome 5. Possible roles include lipid binding, lipid peroxidation recycling, binding the toxin itself (list number of references where this might be the case), altering signaling.

In yeast, trichothecenes appear to modify cell membrane permeability [41]. For instance, an in vitro assay of L-6 mycoblasts in culture, T-2 toxin altered the permeability of cell membranes. The measured effect occurred within 10 minutes of the application of the mycotoxin. The overexpression of LTP4 and/or LTP5 may affect the cuticle lipid composition. Alteration of the cuticle has been shown to enhance disease susceptibility in plants [42]. Deletion of a glycosylphosphatidylinositol-anchored LTP (LTPG1) in *Arabidopsis* led to a more diffuse cuticular layer structure and an increased susceptibility to infection by the fungal pathogen *Alternaria brassicicola [*43].

T-2 toxin affected the permeability of cell membranes of L-6 myoblasts in vitro at concentrations of 0.4 pg/ml. The effect occurred within 10 minutes, indicating that the mechanism is different from inhibition of protein synthesis since most short-lived proteins have half lives measured in hours (Bunner & Morris, 1988). A recent study has shown that less than 10 μmol/ml DON (<0.296 μg/ml) selectively inhibited some intestinal transport proteins in human intestinal epithelial cells when the cells were incubated with the toxin for 24 and 48 hours. The transport of palmitate across the membrane was increased. The effects were mimicked both by cycloheximide, an inhibitor of the protein synthesis, and deoxycholate, an inducer of apoptosis, a finding which according to the authors indicated that inhibition of the protein synthesis and apoptosis are the main mechanisms for DON toxicity in the cells (Maresca et al., 2002). T-2 toxin also caused changes in the phospholipid turnover in bovine platelets (Grandoni et al., 1992) and haemolysis of erythrocytes in vitro (Rizzo et al., 1992; Rizzo et al., 1994). Antioxidants like ascorbic acid, α-tocopherol and selenium (Tutelyan et al., 1990; Rizzo et al., 1994) and glutathione precursors (Fricke & Jorge, 1991) protect against lipid peroxidation induced by trichothecenes in vivo and against the cytotoxicity of T-2 toxin (Shokri et al., 2000).

Lipid transfer proteins (LTPs) were initially defined by their ability to facilitate the transfer of phospholipids between membranes in vitro and in vivo (Kader, 1996). Plant LTPs are small (7-10 kD), abundant, and basic proteins that have a hydrophobic pocket capable of accommodating fatty acids or lysophospholipid molecules (Shin et al., 1995; Beisson et al., 2003). The results of plant genome and EST projects have demonstrated the presence of multiple LTP isoforms, which are speculated to be associated with diverse functions including cutin and wax assembly, pathogen defense, antifreezing, long-distance signaling, and cell wall loosening (Pyee and Kolattukudy, 1995; Molina and Garcî a-Olmedo, 1997; Maldonado et al., 2002; Beisson et al., 2003; Jeroen et al., 2005; Cameron et al., 2006; Roy-Barman et al., 2006; Choi et al., 2008). Most plant LTPs localize to the cell wall, which suggests that LTPs play a role in cutin monomers and wax transport (Pyee and Kolattukudy, 1995). The accumulation of cuticular wax on the leaves of tree tobacco (Nicotiana glauca) and the concomitant increase in LTP expression in response to drought stress indirectly suggest that LTP is involved in the accumulation of wax (Cameron et al., 2006).

Our studies validated activation tagging as an excellent approach to discover novel plant genes for resistance to trichothecenes. The approach provides a method to identify novel and uncharacterized plant genes, like nsLTPs, which provide enhanced resistance to a virulence factors produced by *Fusarium* and likely other genes associated with fungal resistance. Durable FHB resistance in barley and wheat will likely require the pyramiding of several resistance genes. Activation tagging successfully identified two novel and uncharacterized LTP genes whose increased expression provided trichothecene resistance and one novel gene (At5G01620) whose disruption provided trichothecene resistance.

References for Example I

1. Rocha O, Ansari K, Doohan F M (2005) Effects of trichothecene mycotoxins on eukaryotic cells: a review. Food Addit Contam 22: 369-378.
2. McMullen M, Jones R, Gallenberg D (1997) Scab of wheat and barley: A re-emerging disease of devastating impact. Plant Disease 81: 1340-1348.
3. Desjardins A E, Hohn T M, Mccormick S P (1993) Trichothecene Biosynthesis in *Fusarium* Species—Chemistry, Genetics, and Significance. Microbiological Reviews 57: 595-604.
4. Foroud N A, Eudes F (2009) Trichothecenes in Cereal Grains. International Journal of Molecular Sciences 10: 147-173.
5. Peraica M, Radic B, Lucic A, Pavlovic M (1999) Toxic effects of mycotoxins in humans. Bulletin of the World Health Organization 77: 754-766.
6. Fried H M, Warner J R (1981) Cloning of yeast gene for trichodermin resistance and ribosomal protein L3. Proc Natl Acad Sci USA 78: 238-242.
7. Fernandez-Lobato M, Cannon M, Mitlin J A, Mount R C, Jimenez A (1990) Characterization of *Saccharomyces cerevisiae* strains displaying high-level or low-level resistance to trichothecene antibiotics. Biochem J 267: 709-713.
8. Di R, Tumer N E (2005) Expression of a truncated form of ribosomal protein L3 confers resistance to pokeweed antiviral protein and the *Fusarium* mycotoxin deoxynivalenol. Mol Plant Microbe Interact 18: 762-770.
9. Harris L J, Gleddie S C (2001) A modified rpl3 gene from rice confers tolerance of the *Fusarium graminearum* mycotoxin deoxynivalenol to transgenic tobacco. Molecular Plant Pathol 58: 173-181.
10. Mitterbauer R, Poppenberger B, Raditschnig A, Lucyshyn D, Lemmens M, et al. (2004) Toxin-dependent utilization of engineered ribosomal protein L3 limits trichothecene resistance in transgenic plants. Plant Biotechnology J 2: 329-340.
11. Lafarge-Frayssinet C, Decloitre F, Mousset S, Martin M, Frayssinet C (1981) Induction of DNA single-strand breaks by T2 toxin, a trichothecene metabolite of *fusarium*: effect on lymphoid organs and liver. Mutat Res 88: 115-123.
12. Pace J G, Watts M R, Canterbury W J (1988) T-2 mycotoxin inhibits mitochondrial protein synthesis. Toxicon 26: 77-85.
13. Bin-Umer M A, McLaughlin J E, Basu D, McCormick S, Turner N E (2011) Trichothecene mycotoxins inhibit mitochondrial translation—implication for the mechanism of toxicity. Toxins 3: 1484-1501.
14. Schappert K T, Khachatourians G G (1984) Influence of the membrane on T-2 toxin toxicity in *Saccharomyces* spp. Appl Environ Microbiol 47: 681-684.
15. Schappert K T, Khachatourians G G (1986) Effects of T-2 toxin on induction of petite mutants and mitochondrial function in *Saccharomyces cerevisiae*. Current genetics 10: 671-676.
16. McLaughlin J E, Bin-Umer M A, Tortora A, Mendez N, McCormick S, et al. (2009) A genome-wide screen in *Saccharomyces cerevisiae* reveals a critical role for the mitochondria in the toxicity of a trichothecene mycotoxin. Proceedings of the National Academy of Sciences 106: 21883-21888.
17. Bushnell W R, Perkins-Veazie P, Russo V M, Collins J, Seeland T M (2010) Effects of Deoxynivalenol on Content of Chloroplast Pigments in Barley Leaf Tissues. Phytopathology 100: 33-41.
18. Danuta P, Sliwinska E (2005) Trichothecene fusarial toxins perturb the cell cycle in meristematic cells of *Secale cereale* L., *Triticum aestivum* L. and *Vicia faba* L. Caryologia 58: 86-93.
19. Bai G H, Desjardins A E, Plattner R D (2002) Deoxynivalenol-nonproducing *fusarium graminearum* causes initial infection, but does not cause disease spread in wheat spikes. Mycopathologia 153: 91-98.
20. Eudes F, Comeau A, Rioux S, Collin J (2001) Impact of trichothecenes on *Fusarium* head blight [*Fusarium graminearum*] development in spring wheat (*Triticum aestivum*). Canadian Journal of Plant Pathology 23: 318-322.
21. Proctor R H, Hohn T M, Mccormick S P (1995) Reduced Virulence of Gibberella-Zeae Caused by Disruption of a Trichothecene Toxin Biosynthetic Gene. Molecular Plant-Microbe Interactions 8: 593-601.
22. Golkari S, Gilbert J, Prashar S, Procunier J D (2007) Microarray analysis of *Fusarium graminearum*-induced wheat genes: identification of organ-specific and differentially expressed genes. Plant biotechnology journal 5: 38-49.

23. Jia H, Cho S, Muehlbauer G J (2009) Transcriptome analysis of a wheat near-isogenic line pair carrying *Fusarium* head blight-resistant and -susceptible alleles. Molecular plant-microbe interactions: MPMI 22: 1366-1378.
24. Foroud N A, Ouellet T, Laroche A, Oosterveen B, Jordan M C, et al. (2012) Differential transcriptome analyses of three wheat genotypes reveal different host response pathways associated with *Fusarium* head blight and trichothecene resistance. Plant Pathology 61: 296-314.
25. Desjardins A E, McCormick S P, Appell M (2007) Structure-activity relationships of trichothecene toxins in an *Arabidopsis thaliana* leaf assay. Journal of Agricultural and Food Chemistry 55: 6487-6492.
26. Urban M, Daniels S, Mott E, Hammond-Kosack K (2002) *Arabidopsis* is susceptible to the cereal ear blight fungal pathogens *Fusarium graminearum* and *Fusarium culmorum*. Plant Journal 32: 961-973.
27. Pestov D G, Shcherbik N (2012) Rapid Cytoplasmic Turnover of Yeast Ribosomes in Response to Rapamycin Inhibition of TOR. Molecular and Cellular Biology 32: 2135-2144.
28. Weigel D, Ahn J H, Blazquez M A, Borevitz J O, Christensen S K, et al. (2000) Activation tagging in *Arabidopsis*. Plant Physiology 122: 1003-1013.
29. Qu S, Desai A, Wing R, Sundaresan V (2008) A versatile transposon-based activation tag vector system for functional genomics in cereals and other monocot plants. Plant Physiology 146: 189-199.
30. Kardailsky I, Shukla V K, Ahn J H, Dagenais N, Christensen S K, et al. (1999) Activation tagging of the floral inducer FT. Science 286: 1962-1965.
31. Aboul-Soud M A, Chen X, Kang J G, Yun B W, Raja M U, et al. (2009) Activation tagging of ADR2 conveys a spreading lesion phenotype and resistance to biotrophic pathogens. The New phytologist 183: 1163-1175.
32. Ayliffe M A, Pryor A J (2007) Activation tagging in plants—generation of novel, gain-of-function mutations. Australian Journal of Agricultural Research 58: 490-497.
33. Ayliffe M A, Pallotta M, Langridge P, Pryor A J (2007) A barley activation tagging system. Plant molecular biology 64: 329-347.
34. Ayliffe M A, Pryor A J (2011) Activation tagging and insertional mutagenesis in barley. Methods in molecular biology 678: 107-128.
35. Singer T, Burke E (2003) High-throughput TAIL-PCR as a tool to identify DNA flanking insertions. Methods Mol Biol 236: 241-272.
36. Shcherbik N, Wang M S, Lapik Y R, Srivastava L, Pestov D G (2010) Polyadenylation and degradation of incomplete RNA polymerase I transcripts in mammalian cells. Embo Reports 11: 106-111.
37. Gratenstein K, Heggestad A D, Fortun J, Notterpek L, Pestov D G, et al. (2005) The WD-repeat protein GRWD1: Potential roles in myeloid differentiation and ribosome biogenesis. Genomics 85: 762-773.
38. Heazlewood J L, Verboom R E, Tonti-Filippini J, Small I, Millar A H (2007) SUBA: the *Arabidopsis* Subcellular Database. Nucleic acids research 35: D213-218.
39. Zhang X R, Henriques R, Lin S S, Niu Q W, Chua N H (2006) *Agrobacterium*-mediated transformation of *Arabidopsis thaliana* using the floral dip method. Nature Protocols 1: 641-646.
40. Lapik Y R, Fernandes C J, Lau L F, Pestov D G (2004) Physical and functional interaction between pes1 and bop1 in mammalian ribosome biogenesis. Molecular Cell 15: 17-29.
41. Schappert K T, Khachatourians G G (1984) Influence of the membrane on T-2 toxin toxicity in *Saccharomyces* spp. Applied and Environmental Microbiology 47: 681-684.
42. Li Y, Beisson F, Koo A J, Molina I, Pollard M, et al. (2007) Identification of acyltransferases required for cutin biosynthesis and production of cutin with suberin-like monomers. Proceedings of the National Academy of Sciences of the United States of America 104: 18339-18344.
43. Lee S B, Go Y S, Bae H J, Park J H, Cho S H, et al. (2009) Disruption of glycosylphosphatidylinositol-anchored lipid transfer protein gene altered cuticular lipid composition, increased plastoglobules, and enhanced susceptibility to infection by the fungal pathogen *Alternaria brassicicola*. Plant Physiology 150: 42-54.

Example II

In this study, the role of *A. thaliana* derived LTP4 and LTP5 in trichothecene toxicity was investigated. We used the yeast model to show that, similar to their response in *A. thaliana*, overexpression of these two type IV nsLTPs conferred resistance to cells grown against lethal doses of Tcin. Not only was this response unique to these two nsLTPs, this was not seen against other inhibitors of yeast growth. Our results also suggest that mitochondria are likely to play a critical role in nsLTP-mediated resistance to trichothecenes. Yeast cells overexpressing LTP4 and LTP5, in the presence of Tcin, showed little or no inhibition of mitochondrial translation, unlike cytosolic translation which was significantly inhibited. We also showed that reactive oxygen species (ROS) generation, an early time point event during trichothecene toxicity, is alleviated in yeast overexpressing LTP4 and LTP5. Our study, therefore, demonstrates that expression of type IV LTPs confer resistance to trichothecene mycotoxins in yeast and provide insight into the mechanism by which this resistance is attained and the likely role of mitochondria in it.

The following materials and methods are provided to facilitate the practice of Example II.

Yeast Strains and Plasmids

Yeast strain BY4743 (MATa/α, his3Δ1/his3Δ1, leu2Δ0/leu2Δ0, LYS2/lys2Δ0, met15Δ0/MET15, ura3Δ0/ura3Δ0) was used as the background for all experiments. Gateway® entry vector pDONR™221 was purchased from Invitrogen while the destination vector pAG425-GAL1-ccdB-HA (plasmid#14249) was purchased from Addgene® (www.addgene.com).

Gateway Cloning and Yeast Transformation

Standard gateway® cloning procedure was followed to clone the LTP genes into the destination vector, pAG425-GAL1-ccdB-HA. Gateway®-compatible primers were designed to amplify the LTP coding sequences without the stop codon. Using standard PCR protocol, the two nsLTPs were amplified from genomic DNA isolated from *Arabidopsis* seeds. The resulting LTP amplicons with flanking attB1 and attB2 sequences were then cloned into a pDONR™221 vector (Invitrogen) with Gateway®BP Clonase®II Enzyme mix according to manufacturer's protocol. Using Gateway®LR Clonase®II Enzyme mix, LTP4 and LTP5 genes were shuttled from the pDONR™221 entry vector into pAG425-GAL1-ccdB-HA, the destination vector. At the end of BP and LR reactions the resulting product was transformed into DH5-α cells for propagation and verified.

Yeast cells were transformed with the final destination vectors carrying the LTP genes using a standard transformation protocol. The empty backbone vector, pAG425-GAL1-ccdB-HA, was used to transform yeast cells and used as vector control for further experiments.

Trichothecene Isolation

Tcin was isolated from *Trichotheciumroseum* and prepared as described previously.

Growth Assay

Yeast cells carrying the different overexpression vectors were initially grown in synthetic leucine dropout (SD-Leu) media supplemented with 2% raffinose and later shifted to SD-Leu media with 2% galactose for induction of the LTP4 and LTP5 genes. Following induction of the nsLTP genes for (3 to 6 h) equal amounts of cells were added to standard microplates (24-well or 96-well) containing SD-Leu with 2% galactose.

Tcin, cycloheximide, anisomycin, and chloramphenicol were added to the final concentrations as specified. The plates were sealed with breathable strips and growth at $OD_{600}$ was recorded every 30-60 minutes for a period of 36-48 hours shaking constantly at 30° C. in a BioTek® plate reader.

Analysis of Total Translation

Cells grown in SD-Leu (+2% Raffinose) were shifted to synthetic methionine dropout (SD-Met) media (Yeast Nitrogen Base w/o Amino Acids & Ammonium Sulfate, all amino acids except methionine) containing MSG as the nitrogen source and 2% galactose for 3 hours. Cultures grown to an OD600 of 0.2-0.3 were then split into two: one-half was treated with a range of increasing concentrations of Tcin (0-4 μM) in ethanol and the other half was treated with an equivalent amount of ethanol. Following one hour treatment with Tcin at 30° C., 3 $OD_{600}$ cells were washed with minimal media by a quick spin (10,000 g for 1 min) and resuspended in 500 μL SD-Met (+2% raffinose). To each sample, 1 μL [$^{35}$S]-Met (Perkin-Elmer, NEG-009A, >1000 Ci/mmol) was added. The reaction was stopped after 20 min by washing and resuspending cells in 500 μL (20 mM) cold methionine and 75 μL Rodel Mix (560 μL 5 M NaOH, 0.11 mL β-mercaptoethanol, 0.76 mL $H_2O$, 0.075 mL 1 mM PMSF). An equal volume of 50% TCA (trichloroacetic acid) was added to the mix and filtered through 2.4 cm glass fiber filters (grade 691, VWR). Filters were then washed, twice each, with 5% TCA and 95% ethanol and scintillation counts per minute (CPM) measured. CPM readings were finally normalized to OD600 to indicate total translation.

Analysis of Mitochondrial Translation

The mitochondrial translation assay was done as the total translation assay with the following exception: Prior to the addition of [35S]-Met, 20 μL (7.5 mg/mL) freshly prepared cycloheximide was added to each sample to selectively inhibit cytosolic translation and incubated for 5 min.

Flow Cytometry

Trichothecene-treated and untreated cells were stained with 2',7'-dichlorfluorescein-diacetate (DCFH-DA) for ROS generation and MitoTracker Red CMXRos for mitochondrial membrane potential according to manufacturer's protocol. Following staining with the appropriate dyes, cells were analyzed using the Accuri C6 Flow Cytometer® (Accuri Cytometers Inc., Ann Arbor, Mich.). For each sample 15,000 events were recorded. Channel gating and histogram plots were made using the CFlowPlus Analysis software (Accuri Cytometers Inc, Ann Arbor, Mich.). Changes in MitoTracker Red and DCFH-DA fluorescence were detected using the FL1 and FL3 channel respectively.

Data Analysis & Graphing

Data from the growth and translation assays were analyzed and the graphs were plotted using Microsoft Excel.

Figure 9:
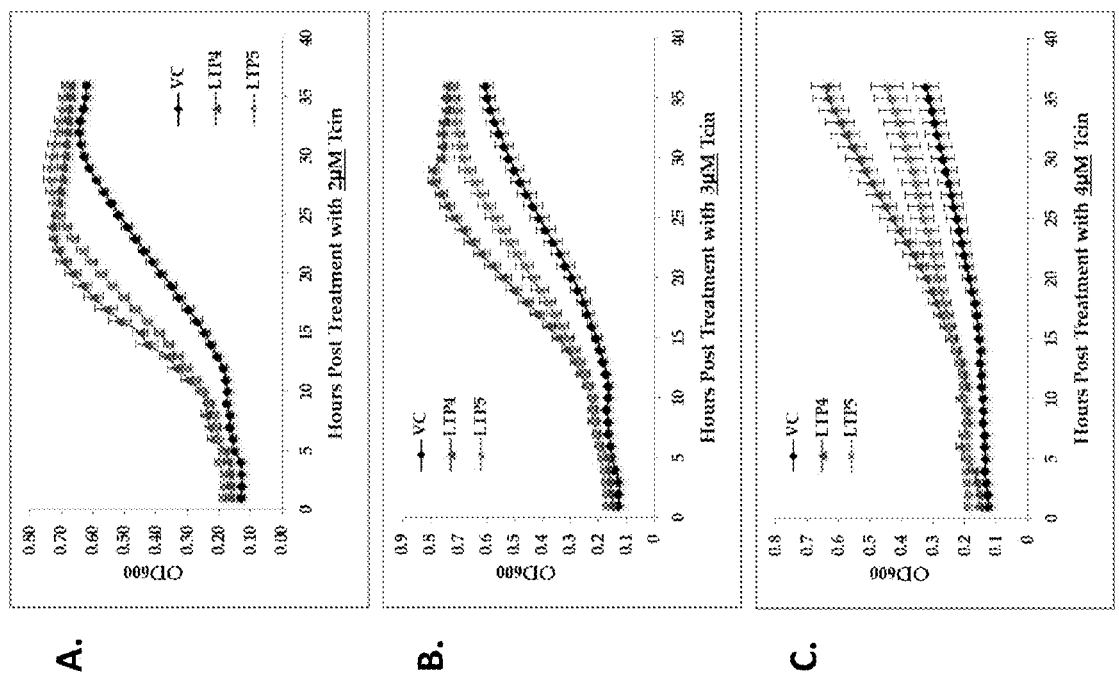
FIG. 9. Growth of BY4743 overexpressing At. LTP4 and LTP5 against Tcin: BY4743 cells overexpressing HA-tagged LTP4 and LTP5 were treated with 2 µM Tcin (A), 3 µM Tcin (B) and 4 µM (C) for 36 h. OD600 readings were recorded at every 60 min. with continuous shaking at 30° C. in a BioTek (Synergy) plate reader. Error bars indicate S.E where n=3 independent replicates.

Results:

Wild type (BY4743) yeast cells overexpressing LTP4 and LTP5 were grown in selective media containing galactose against increasing concentrations of Tcin (FIG. 9). A shift in sensitivity, in the growth curves of cells overexpressing LTP4 and LTP5, was evident at 2 μM Tcin (FIG. 9A). Relative to growth of cells containing the vector alone, LTP4 and LTP5 overexpression provided resistance to yeast cells against Tcin. This tolerance to Tcin was enhanced further against 3 μM (FIG. 1B) and 4 μM (FIG. 1C) concentrations. It is interesting to note that in almost all instances, LTP4 overexpressing cells consistently had a relatively better growth against Tcin, when compared to cells overexpressing LTP5.

Figure 10:
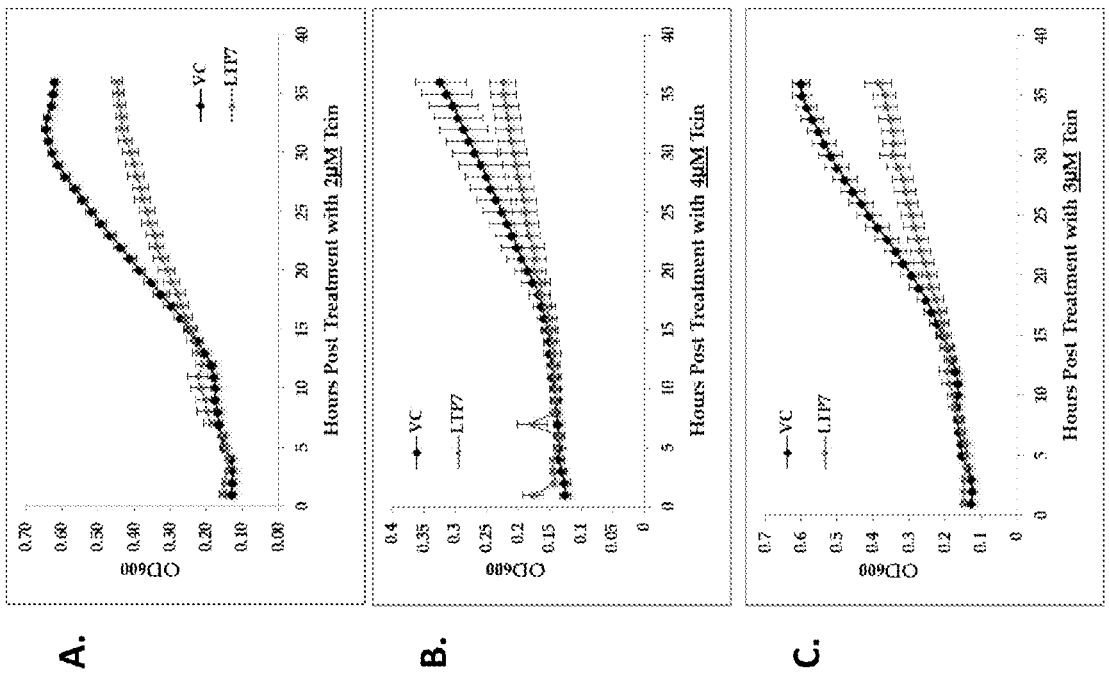
FIG. 10. Growth of BY4743 overexpressing At. LTP1.1 against Tcin: BY4743 cells overexpressing HA-tagged LTP1.1 were treated with 2 µM Tcin (A), 3 µM Tcin (B) and 4 µM (C) for 36 h. OD600 readings were recorded at every 60 min. with continuous shaking at 30° C. in a BioTek (Synergy) plate reader. Error bars indicate S.E where n=3 independent replicates.
Figure 11:
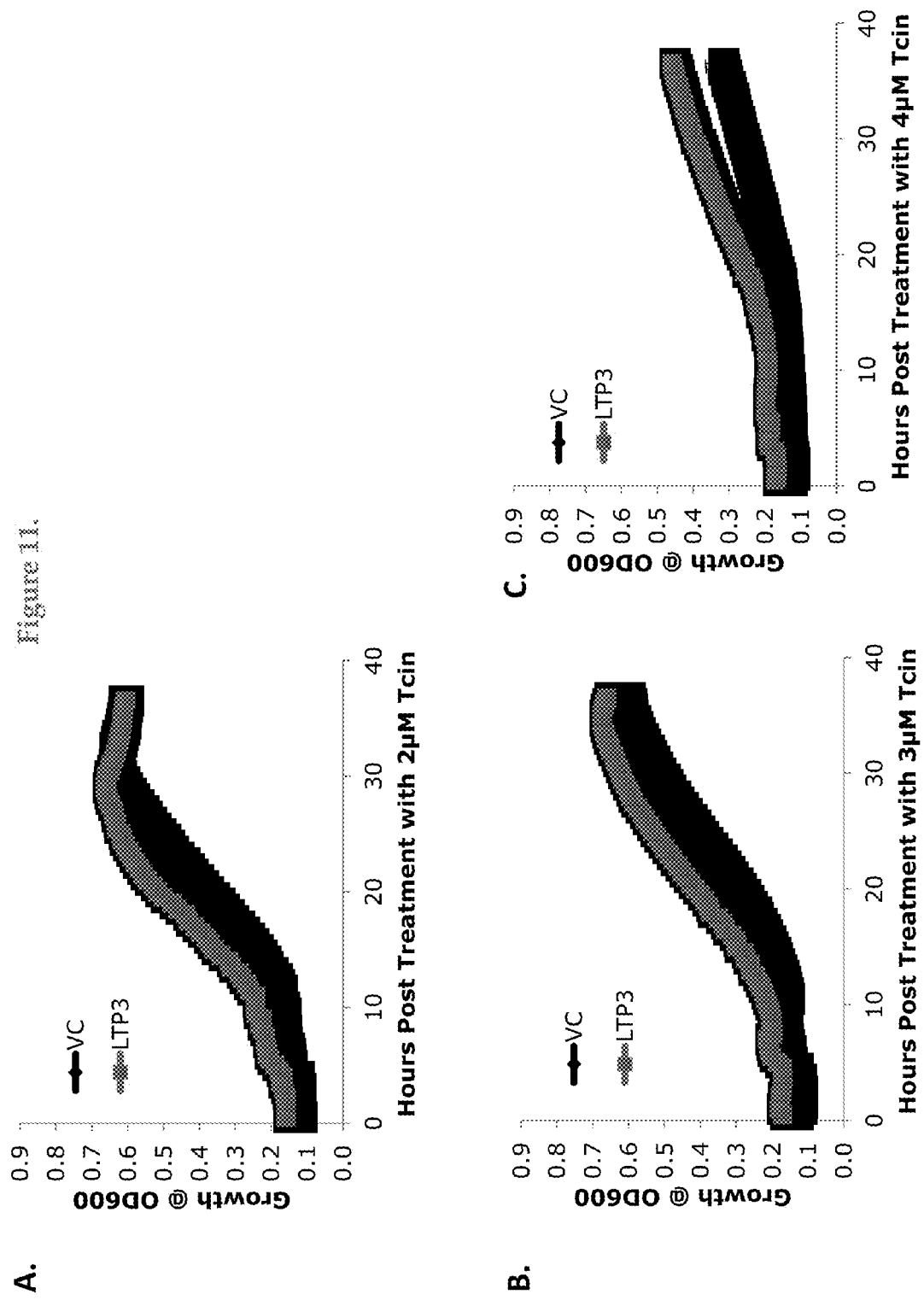
FIG. 11. Growth of BY4743 overexpressing Ta. LTP3 against Tcin: BY4743 cells overexpressing HA-tagged Ta. LTP3 were treated with 2 µM Tcin (A), 3 µM Tcin (B) and 4 µM (C) for 36 h. OD600 readings were recorded at every 60 min. with continuous shaking at 30° C. in a BioTek (Synergy) plate reader. Error bars indicate S.E where n=3 independent replicates.

This enhanced growth in the presence of sub-lethal to lethal doses of Tcin was not observed with cells overexpressing LTP1.1, a type I nsLTP also derived from *A. thaliana* (FIG. 10). LTP1.1, like several type I nsLTPs, has high sequence homology to classical LTPs which contain the hydrophobic tunnel necessary for transferring lipids between membranes. Interestingly, overexpressing LTP1.1 rendered the cells more sensitive to Tcin, when compared to the growth of cells carrying the vector alone. Thus not all nsLTPs, upon overexpression, confer resistance to trichothecenes. Recently, Foroud et al. used transcriptome profiling to identify different host response pathways associated with FHB [23]. Constitutive differences in gene expression between the FHB-resistant and susceptible cultivars, when compared, revealed the overexpression of LTP3, a type I lipid transfer protein in the resistant cultivar. When we transformed yeast cells to overexpress this Ta. LTP3 they were increasingly resistant to Tcin (FIG. 11) suggesting that like LTP4 and LTP5 from *A. thaliana*, overexpression of Ta. LTP3 also enhanced tolerance Tcin in yeast. Since LTPs from different plant sources were able to provide resistance to Tcin in yeast it is likely that the *Arabidopsis* LTP4 and LTP5 and the wheat LTP3 directly participate in resistance, rather than in inducing signaling.

Tcin, like other trichothecenes, has been previously identified as a potent inhibitor of protein synthesis, which in turn affects the growth of cells. Hence, we looked at the effect of LTP4 and LTP5 overexpression on the growth of yeast against various inhibitors of translation and growth. Cycloheximide and anisomycin are known inhibitors of cytosolic protein synthesis while chloramphenicol inhibits only the mitochondrial protein synthesis and all three antibiotics have been previously shown to inhibit yeast growth at varying concentrations. When cells overexpressing LTP4 and LTP5 were grown against 7.5 μg/mL anisomycin (FIG. 12A), 0.25 μg/mL cycloheximide (FIG. 12B) or 5 mg/mL chloramphenicol (FIG. 12C) no significant shift in growth sensitivity was observed relative to cells carrying the vector alone (FIG. 12). Since LTP4 and LTP5 did not provide any resistance to yeast cells against any of these inhibitors, resistance to Tcin is likely to be a very specific response that is unique to these two type IV nsLTPs.

The current classifications of nsLTPs in to the nine different types are based on sequence homology and phylogenetic analysis [12, 13]. Bioinformatics studies reveal that all nsLTPs have an N-terminal signal peptide and the length of the mature proteins vary even within a particular group [12]. However, not much is known about the manner in which these proteins are processed in vivo or about their localization in the cell. Previously we pointed to the interesting observation that, between LTP4 and LTP5, cells overexpressing LTP4 had a better growth against Tcin. Could this possibly be attributed to differences in the expression or localization of the two proteins? To answer these questions we performed sucellular fractionation of yeast cells overexpressing LTP4 and LTP5. Since the proteins were expressed as a fusion protein with an HA tag, following separation on a 15% SDS-PAGE gel, we used anti-HA antibody to immunostain and identify the presence of LTP4 and LTP5 in the different cell fractions. The 11 kDa LTP5 and 11.7 kDA LTP5 proteins appeared to be processed differently (FIG. 5). The three forms of LTP5, as revealed by HA-immunostaining, could most likely be the pre-protein (high MW band), mature protein and another spliced variant (low MW band). LTP4 on the other hand seems to exist only as the mature protein as indicated by the single band. Furthermore, LTP4 was largely associated with the cytosolic fraction (FIG. 13A) unlike LTP5, which appeared largely in the membrane fraction (FIG. 13B). These results indicate that not only are LTP4 and LTP5 processed differently in vivo but they also localize differently, with LTP5 most likely utilizing the secretory pathway.

Figure 14:
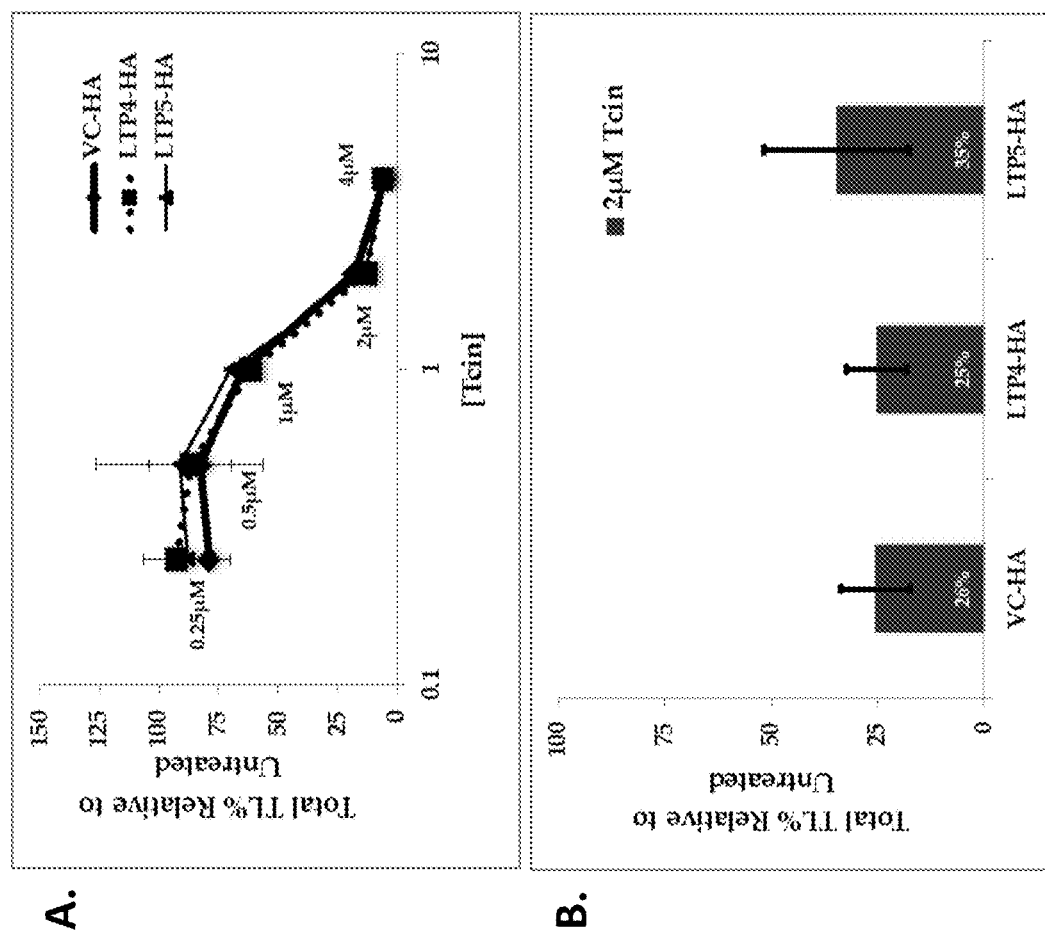
FIG. 14. Effect of Tcin on total translation in yeast cells overexpressing LTP4 & LTP5: (A) BY4743 overexpressing LTP4 and LTP5 were with increasing concentrations of Tcin. Following the 1 h post treatment with Tcin, [$^{35}$S]-methionine incorporation was measured for 20 min. and rate of translation calculated as described in Materials and Methods. (B) Total translation in the same cells at 2 µM Tcin. Final counts (CPM) for all experiments were normalized to the OD600 of each sample. Translation levels of trichothecene-treated samples were expressed as a percentage of the control samples set to 100%. Error bars indicate S.E. where n=3 independent replicates.

Since protein synthesis is a known and well characterized target of trichothecenes [5] we asked whether the efficiency of translation is altered in Tcin-treated yeast overexpressing LTP4 and LTP5. At a range of different concentrations varying from 0 to 4 µM Tcin we assayed the rate of in vivo total translation in these cells. As expected, Tcin inhibited total translation with increasing concentrations in cells carrying the vector alone (FIG. 14A). However, a similar drop in the efficiency of total translation, due to Tcin treatment, was also seen with cells overexpressing LTP4 and LTP5. At 2 µM Tcin, total translation was inhibited in all cells by 75% or higher (FIG. 14B) suggesting that cytosolic protein synthesis is not protected against Tcin in cells overexpressing LTP4 and LTP5 and therefore not likely attributed to the observed resistance.

Figure 15:
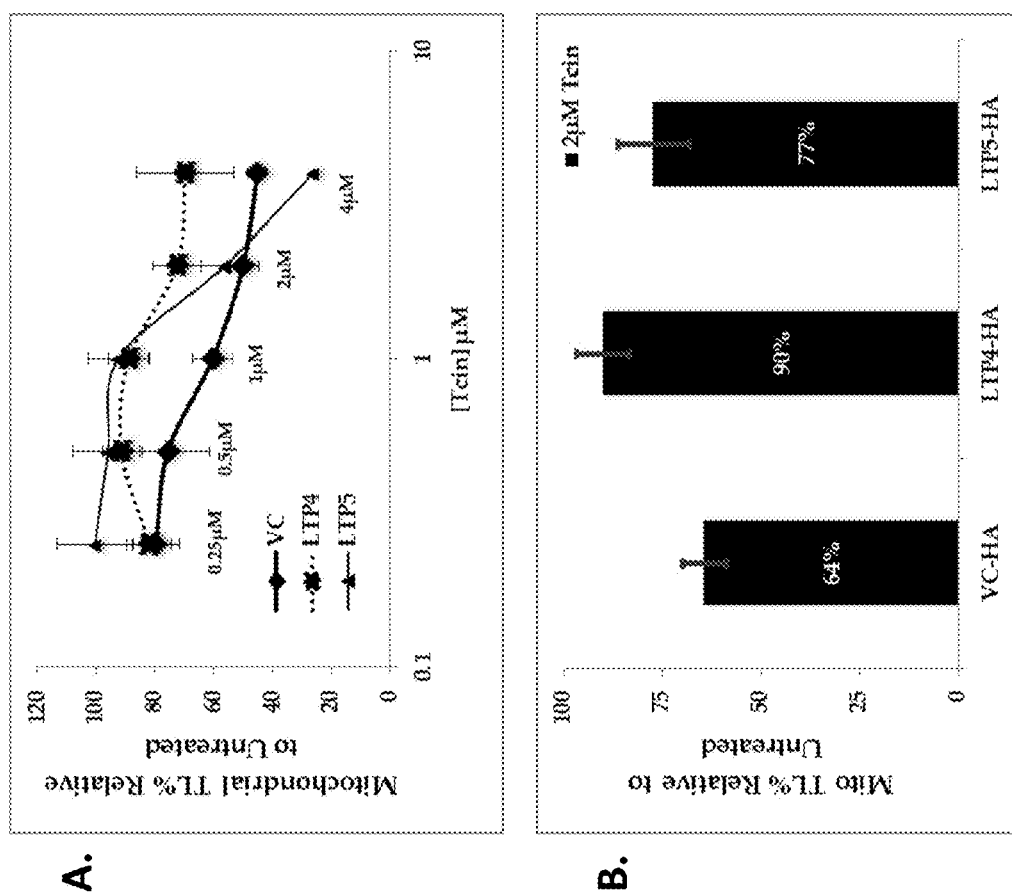
FIG. 15. Effect of Tcin on mitochondrial translation in yeast cells overexpressing LTP4 & LTP5: (A) BY4743 overexpressing LTP4 and LTP5 were with increasing concentrations of Tcin for 1 h. Prior to measuring [35S]-methionine incorporation cytosolic translation was stopped with cycloheximide. (B) Mitochondrial translation in the same cells at 2 µM Tcin. Final counts (CPM) for all experiments were normalized to the OD600 of each sample. Translation levels of trichothecene-treated samples were expressed as a percentage of the control samples set to 100%. Error bars indicate S.E. where n=3 independent replicates.

In addition to cytosolic protein synthesis, the mitochondrion also houses a translation machinery that is very similar to the prokaryotic ribosomes. Previously, we had shown that not only is mitochondrial translation inhibited by Tcin but is also a primary target [24]. Hence, we looked at the rate of mitochondrial translation in intact cells overexpressing LTP4 and LTP5 when grown against Tcin (FIG. 15). Mitochondrial translation was inhibited with increasing concentrations of Tcin in cells carrying the vector alone (FIG. 15A). However, this inhibition was moderated significantly in cells overexpressing LTP4 and LTP5 (FIG. 15A). Unlike cytosolic translation, which was inhibited by more than 75% in all cells, at 2 µMTcin (FIG. 14B), mitochondrial translation was only inhibited by 10% and 23% in cells overexpressing LTP4 and LTP5 respectively, while in cells carrying the vector alone, this inhibition increased to 36% (FIG. 14B). These results suggest that inhibition of mitochondrial translation by Tcin is lessened by the overexpression of the two type IV nsLTPs.

Mitochondria have been shown to play a critical role in trichothecene toxicity [7, 24-26]. These earlier studies have implicated mitochondrial translation, morphology, membrane potential and ROS generation to be key players during trichothecene-mediated cell death. Our earlier studies revealed that many of these targets are not secondary to cytosolic translation [24] but often early time point targets during trichothecene toxicity. One such early time point event, that occurs in yeast cells treated with Tcin, is the generation of reactive oxygen species (ROS) [27]. Like other trichothecenes, Tcin has been shown to promote ROS generation early on but drops during the later stages due to dissipation of the mitochondrial membrane potential ($\psi_{mito}$) [24]. Both $\psi_{mito}$ and ROS generation were measured in cells overexpressing LTP4 and LTP5 in the presence of Tcin to determine whether these two biomarkers for functional mitochondria were altered. Thus, cells were stained with MitoTracker Red (MTR) and DCHF-DA for measuring $\psi_{mito}$ and ROS generation respectively. While MTR is a fluorescent dye that selectively enters mitochondria with an active potential, DCFH-DA only fluoresces upon contact with ROS. When treated with increasing concentrations of Tcin, although $\psi_{mito}$ did not change much (FIG. 16A), the number of cells producing ROS varied significantly (FIG. 16B) among the three types of cells. A relatively higher number of cells produced ROS in cells carrying the vector alone even prior to Tcin treatment. Within 20 minutes of treatment with Tcin, cells producing ROS increased from 3% (0 µM) to over 5% (1 µM and 2 µM). However, in cells overexpressing LTP4 and LTP5 less than 2% of the cells produced ROS regardless of Tcin treatment. Thus, Tcin-mediated ROS generation is relatively reduced in cells overexpressing LTP4 and LTP5, which in turn could possibly enhance the cells' tolerance to the toxin.

Discussion:

Our present work has attempted to investigate the mechanisms by which a set of nonspecific lipid transfer proteins (nsLTP) mediate resistance to trichothecenes in yeast and by extension in higher eukaryotes including economically important cereal crops like wheat and barley. Only recently have nsLTPs been the focus of novel approaches to enhancing resistance to FHB and trichothecene toxicity. Earlier studies had identified the intrinsic antibacterial and antifungal properties of nsLTPs isolated from several different plants, including Ace-AMP1, which inhibited the growth of over 12 different fungi and several gram positive bacteria [17]. Later, Molina et al. showed that transgenic expression of barley LTP2 enhanced tolerance to the pathogen P. syringae [28]. Also, another LTP, Ha-AP10, was shown to completely inhibit the germination of F. solani spores via membrane permeabilization[29]. More recently, Zhu, X et al. showed that overexpression of Ta. LTP5 provided increased resistance to F. graminearum in transgenic wheat [30]. In all these and other earlier studies, however, the nsLTPs were tested against the pathogens including Fusarium spp. but not the toxins. Furthermore, although these nsLTPs were shown to provide resistance not much was investigated about their mechanism of action. Hence how these nsLTPs provide resistance to Fusarium pathogenesis or trichothecene toxicity is very crucial and remains to be fully understood.

Recently, Masuda et al. had shown that when T-2 toxin, a type A trichothecene, was applied to the shoots of A. thaliana plants, LTP1.5, a type I nsLTP gene, was upregulated[31]. Furthermore, in our activation tagged screening of A. thaliana seeds for Tcin resistance, we identified two type IV nsLTP genes, LTP4 and LTP5, to be overexpressed. These and other earlier studies[32] suggest that nsLTPsare important in the plant's defense system against Fusarium infection and phytotoxic effects of trichothecenes. Enhancing the plant's defenses can therefore minimize pathogen infection and subsequent contamination of mycotoxins and thereby prevent outbreaks of diseases such as FHB and the ensuing detrimental effects on the global food supply.

Yeast has been previously used as a model to study the mechanism of trichothecene toxicity [7, 24, 33]. In this study, we used yeast to elucidate the mechanism by which plant nsLTPs confer trichothecene resistance and showed that the three different plant LTPs participate directly in resistance. Tcin, unlike DON, is very toxic to yeast cells with an $IC_{50}$ value of only 2.5 µM and earlier studies have thus used Tcin as a representative type B trichothecene to gain insight into the mechanism of action of DON and other type B toxins associated with FHB[7, 24]. Hence to identify novel genes that can mediate resistance to FHB and trichothecene contamination we used Tcin in our activation tagged screening of *A. thaliana* seeds. Although the nsLTPs were derived from *A. thaliana*, not only were the two nsLTP genes expressed in yeast but the overexpression of both LTP4 and LTP5 in yeast agreed with results from our activation tagged screening. This further validates the use of yeast as a potential tool to investigate the underlying molecular mechanisms of FHB and trichothecene toxicity.

Results from our yeast growth assays in which LTP4 and LTP5 genes were overexpressed suggest that the observed resistance with the type IV nsLTPs (FIG. 9) is not specific to plants and that a conserved cellular mechanism is utilized by these low MW proteins in mediating resistance against Tcin. However, we also found that not all nsLTPs have this property since, the type I nsLTP gene, LTP1.1, did not confer resistance against Tcin upon overexpression (FIG. 10). LTP1.5, another type I nsLTP1, was shown to be upregulated in *A. thaliana* shoots injected with T-2 toxin [31]. Thus other *A. thaliana* derived nsLTPs need to be investigated to determine if their overexpression might also provide resistance, similar to LTP4 and LTP5, against trichothecenes. Since lipid transfer proteins are often secreted and found to be associated with the plant cell, it is possible for the cell membranes to be altered upon overexpression of these proteins. Hence the observed resistance against Tcin in LTP4 and LTP5 overexpressing cells could be due to such a cell membrane modification that affected the entry of the small molecule Tcin into the cell. However, this does not seem to be the case since growth of these nsLTP overexpressing cells were significantly inhibited by antibiotics, with varied modes of action, like cycloheximide, anisomycin and chloramphenicol (FIG. 12). The type IV nsLTP mediated resistance against Tcin that we observed in yeast is therefore a specific response that is, thus far, unique to LTP4 and LTP5.

Figure 13:
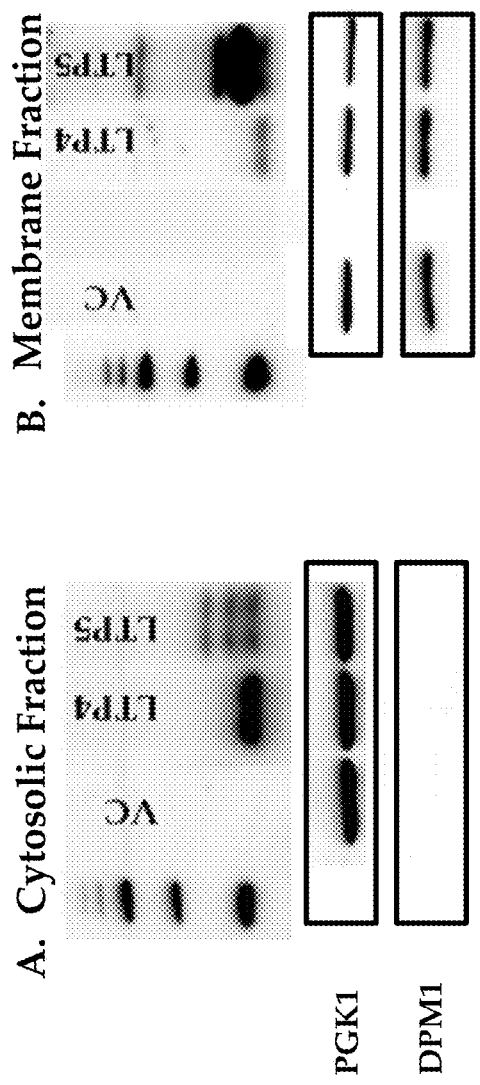
FIG. 13. Isolation of cellular fractions of BY4743 overexpressing LTP4, and LTP5: BY4743 cells overexpressing HA-tagged LTP4 (11 KDa) and LTP5 (11.7 KDa) were induced for 6 h prior to isolation and separation of cytosolic (A), and membrane (B) fractions. Lower panels indicate loading controls Pgk1 for A, and Dpm1 for B. Following SDS-PAGE (15%) and western blotting membranes were immunostained with HA mAb and then with Pgk1 (44.74 KDa) or Dpm1 (30.36 KDa). Membranes stained with HA mAB were photographed after exposing for 156 s (A), and 131 s (B). Pgk1 stained membranes were exposed for 226 s and Dpm1 stained membranes for 526 s.

Despite LTP4 and LTP5 being of plant origin their mature forms were expressed in yeast (FIG. 13). Although expressed in similar levels, the localization of the two proteins varied greatly as seen by subcellular fractionation (FIG. 13). Sequence analysis did not reveal any putative glycosylation sites for LTP5 hence the three different sizes detected could not have been glycosylated forms of the protein. It is possible that not all the LTP5 expressed in the cell is efficiently processed like LTP4, which in turn could also possibly explain the higher, albeit small, resistance seen with cells overexpressing LTP4 relative to LTP5. Despite both nsLTPs containing an N-terminal signal sequence only LTP5 was found to be predominantly associated with membrane fractions (FIG. 13B). Whether this difference, in processing or their abundance in cytosol, can be attributed to the difference in the degree of resistance against Tcin needs to be further investigated. All nsLTPs, studied thus far, are known to be associated with cell wall in plants and are often secreted from the cell [34]. Interestingly, we found LTP4 and LTP5 to be secreted from yeast cells upon overexpression (data not shown). Secretion of the antifungal nsLTPs is likely to serve in the plant's first line of defense by inhibiting hyphal growth, as seen with Ha-AP10, and thereby prevent colonization of the fungal pathogen[20]. However, with trichothecenes, unlike the toxin producing pathogen, the primary site of action of nsLTPs is likely inside the cell since the toxins themselves target cellular processes like protein synthesis and mitochondrial functions. The inhibitory effects of Tcin on mitochondria, the ensuing ROS cascade (FIG. 16B) and the severely affected mitochondrial translation (FIG. 15) are attenuated by LTP4 and LTP5 overexpression. It is, however, also possible for the nsLTPs to have a direct effect on the toxins and thereby either detoxifying trichothecenes via modification of the functional moieties like the acyltransferase protein AYT1[35] or by binding the toxin and preventing it from targeting mitochondria and other cellular targets to induce cell death. Investigating direct interactions between the two nsLTPs and trichothecenes should answer these questions.

Recent changes in world climate and different cultural practices in harvesting have promoted the growth of *F. graminearum* and a reemergence of FHB in several regions posing great challenges to the agriculture and cattle industries[36]. Furthermore, in the absence of uniform global regulatory standards, the worldwide food supply risks introduction of contaminated food grains and the detrimental consequences associated with trichothecene toxicoses [37]. Hence, interest in understanding the underlying mechanisms of trichothecene toxicity to improve resistance to *F. graminearum* infection, FHB and trichothecene contamination have been on the rise. Identifying and characterizing the mechanism of action of trichothecenes at the cellular level might prove an effective approach to developing varied strategies to minimize and eradicate trichothecene-associated diseases like FHB.

nsLTPs present a promising alternative and highly effective solution to current approaches in engineering resistance to FHB and reducing trichothecene contamination. Unlike other defense proteins, nsLTPs are not phytotoxic and hence they can be overexpressed without affecting the plant physiology[15, 34]. To date, several nsLTPs have been implicated in providing resistance to plants from *Arabidopsis* to wheat against different pathogens including *F. graminearum*[19, 30]. However, the mechanism by which these nsLTPs mediated trichothecene resistance remained largely unclear. Our work has utilized yeast to study the mechanism of action of two *A. thaliana* derived nsLTPs, LTP4 and LTP5 and identified mitochondria to play a critical role. Findings from these studies can provide valuable insights into the general mechanism of action of lipid transfer proteins and how these antifungal defense proteins can be employed in engineering resistance in higher plants like wheat and barley against FHB and trichothecene toxicity.

References for Example II

1. Desjardins, A. E., T. M. Hohn, and S. P. McCormick, *Trichothecene biosynthesis in Fusarium species: chemistry, genetics, and significance*. Microbiological reviews, 1993. 57(3): p. 595-604.
2. Etzel, R. A., *CONTEMPO UPDATES: LINKING EVIDENCE AND EXPERIENCE-Mycotoxins*. JAMA-Journal of the American Medical Association-International Edition, 2002. 287(4): p. 425-427.
3. McCormick, S. P., et al., *Trichothecenes: from simple to complex mycotoxins*. Toxins, 2011. 3(7): p. 802-814.
4. Mesterházy, Á., *Role of deoxynivalenol in aggressiveness of Fusarium graminearum and F. culmorum and in resistance to Fusarium head blight*. European Journal of plant pathology, 2002. 108(7): p. 675-684.
5. Cundliffe, E. and J. E. Davies, *Inhibition of initiation, elongation, and termination of eukaryotic protein synthesis by trichothecene fungal toxins*. Antimicrobial agents and chemotherapy, 1977. 11(3): p. 491-499.

6. Rocha, O., K. Ansari, and F. Doohan, *Effects of trichothecene mycotoxins on eukaryotic cells: a review*. Food Additives and Contaminants, 2005. 22(4): p. 369-378.
7. McLaughlin, J. E., et al., *A genome-wide screen in Saccharomyces cerevisiae reveals a critical role for the mitochondria in the toxicity of a trichothecene mycotoxin*. Proceedings of the National Academy of Sciences, 2009. 106(51): p. 21883-21888.
8. Alexander, N., *The TRI101 story: engineering wheat and barley to resist Fusarium head blight*. World Mycotoxin Journal, 2008. 1(1): p. 31-37.
9. Collinge, D. B., et al., *Engineering pathogen resistance in crop plants: current trends and future prospects*. Annual review of phytopathology, 2010. 48: p. 269-291.
10. Dahleen, L. S., P. A. Okubara, and A. E. Blechl, *Transgenic approaches to combat Fusarium head blight in wheat and barley*. Crop science, 2001. 41(3): p. 628-637.

11. Weigel, D., et al., *Activation tagging in Arabidopsis*. Plant Physiology, 2000. 122(4): p. 1003-1014.

12. Boutrot, F., N. Chantret, and M. F. Gautier, *Genome-wide analysis of the rice and Arabidopsis non-specific lipid transfer protein (nsLtp) gene families and identification of wheat nsLtp genes by EST data mining*. BMC genomics, 2008. 9(1): p. 86.

13. José-Estanyol, M., F. X. Gomis-Rüth, and P. Puigdomènech, *The eight-cysteine motif, a versatile structure in plant proteins*. Plant Physiology and Biochemistry, 2004. 42(5): p. 355-365.

14. KADER, J. C., M. JULIENNE, and C. VERGNOLLE, *Purification and characterization of a spinach-leaf protein capable of transferring phospholipids from liposomes to mitochondria or chloroplasts*. European Journal of Biochemistry, 2005. 139(2): p. 411-416.

15. Blein, J. P., et al., *From elicitins to lipid-transfer proteins: a new insight in cell signalling involved in plant defense mechanisms*. Trends in plant science, 2002. 7(7): p. 293-296.

16. Wang, S. Y., et al., *A non-specific lipid transfer protein with antifungal and antibacterial activities from the mung bean*. Peptides, 2004. 25(8): p. 1235-1242.

17. Cammue, B. P. A., et al., *A potent antimicrobial protein from onion seeds showing sequence homology to plant lipid transfer proteins*. Plant Physiology, 1995. 109(2): p. 445-455.

18. Isaac Kirubakaran, S., et al., *Characterization of a new antifungal lipid transfer protein from wheat*. Plant Physiology and Biochemistry, 2008. 46(10): p. 918-927.

19. Molina, A., A. Segura, and F. García-Olmedo, *Lipid transfer proteins (nsLTPs) from barley and maize leaves are potent inhibitors of bacterial and fungal plant pathogens*. FEBS letters, 1993. 316(2): p. 119-122.

20. Regente, M. C. and L. De La Canal, *Purification, characterization and antifungal properties of a lipid-transfer protein from sunflower (Helianthus annuus) seeds*. Physiologia Plantarum, 2001. 110(2): p. 158-163.

21. Maldonado, A. M., et al., *A putative lipid transfer protein involved in systemic resistance signalling in Arabidopsis*. Nature, 2002. 419(6905): p. 399-403.

22. Asero, R., et al., *Lipid transfer protein: a pan-allergen in plant-derived foods that is highly resistant to pepsin digestion*. International archives of allergy and immunology, 2000. 122(1): p. 20-32.

23. Foroud, N., et al., *Differential transcriptome analyses of three wheat genotypes reveal different host response pathways associated with Fusarium head blight and trichothecene resistance*. Plant Pathology, 2011. 61(2): p. 296-314.

24. Bin-Umer, M. A., et al., *Trichothecene Mycotoxins Inhibit Mitochondrial Translation—Implication for the Mechanism of Toxicity*. Toxins, 2011. 3(12): p. 1484-1501.

25. Pace, J., M. Watts, and W. Canterbury, *T-2 mycotoxin inhibits mitochondrial protein synthesis*. Toxicon, 1988. 26(1): p. 77-85.

26. Zhou, H. R., Z. Islam, and J. J. Pestka, *Induction of competing apoptotic and survival signaling pathways in the macrophage by the ribotoxic trichothecene deoxynivalenol*. Toxicological Sciences, 2005. 87(1): p. 113-122.

27. Chaudhari, M., et al., *Oxidative stress induction by T-2 toxin causes DNA damage and triggers apoptosis via caspase pathway in human cervical cancer cells*. Toxicology, 2009. 262(2): p. 153-161.

28. Molina, A. and F. García-Olmedo, *Enhanced tolerance to bacterial pathogens caused by the transgenic expression of barley lipid transfer protein LTP2*. The Plant Journal, 2003. 12(3): p. 669-675.

29. Regente, M., et al., *The cytotoxic properties of a plant lipid transfer protein involve membrane permeabilization of target cells*. Letters in applied microbiology, 2005. 40(3): p. 183-189.

30. Zhu, X., et al., *Overexpression of wheat lipid transfer protein gene TaLTP5 increases resistances to Cochliobolus sativus and Fusarium graminearum in transgenic wheat*. Functional & integrative genomics, 2012: p. 1-8.

31. Masuda, D., et al., *Phytotoxic effects of trichothecenes on the growth and morphology of Arabidopsis thaliana*. Journal of experimental botany, 2007. 58(7): p. 1617-1626.

32. Petti, C., M. Khan, and F. Doohan, *Lipid transfer proteins and protease inhibitors as key factors in the priming of barley responses to Fusarium head blight disease by a biocontrol strain of Pseudomonas fluorescens*. Functional & integrative genomics, 2010. 10(4): p. 619-627.

33. Madhyastha, M., R. Marquardt, and D. Abramson, *Structure-activity relationships and interactions among trichothecene mycotoxins as assessed by yeast bioassay*. Toxicon, 1994. 32(9): p. 1147-1152.

34. Carvalho, A. O. and V. M. Gomes, *Role of plant lipid transfer proteins in plant cell physiology—a concise review*. Peptides, 2007. 28(5): p. 1144-1153.

35. Alexander, N. J., S. P. McCormick, and T. M. Hohn, *The identification of the Saccharomyces cerevisiae gene AYT1 (ORF-YLL063c) encoding an acetyltransferase*. Yeast, 2002. 19(16): p. 1425-1430.

36. McMullen, M., R. Jones, and D. Gallenberg, *Scab of wheat and barley: a re-emerging disease of devastating impact*. Plant disease, 1997. 81(12): p. 1340-1348.

37. Cardwell, K., et al., *Mycotoxins: The cost of achieving food security and food quality*. APSnet. American Phytopathological Society. August, 2001.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A transgenic plant which exhibits increased resistance to a disease caused by a mycotoxin-producing fungus, wherein the plant contains at least one exogenous nucleic acid selected from a) a first exogenous nucleic acid containing a promoter functional in the plant operably linked to SEQ ID NO: 1; and b) a second exogenous nucleic acid that contains a promoter functional in the plant operably linked to SEQ ID NO: 2.

2. The transgenic plant of claim 1, wherein said mycotoxin is a trichothecene.

3. The transgenic plant of claim 2, wherein said trichothecene is selected from the group consisting of trichodermin, deoxynivalenol, diacetoxyscirpeol, zearalenone, nivalenol, 3-acetyldeoxynivalenol, 15-acetyldeoxynivalenol, fusarenon-X, T-2 toxin, and trichothecin (T-cin).

4. The transgenic plant of claim 1, which is a monocot plant.

5. The transgenic plant of claim 1, which is a cereal crop plant.

6. The transgenic plant of claim 1, wherein the cereal crop plant is maize, rice, oat, barley or wheat.

7. The transgenic plant of claim 1, which is a dicot plant.

8. The transgenic plant of claim 1, wherein the promoter and exogenous nucleic acid are non-native to the plant and said promoter causes over-expression of the exogenous nucleic acid to a level greater than nativc levels observed plants lacking said exogenous nucleic acid.

9. The transgenic plant of claim 8, wherein the promoter is selected from a CaMV35S promoter, a ubiquitin promoter, and a PR-1 promoter.

10. An isolated or purified DNA molecule comprising a promoter functional in a plant operably linked to SEQ ID NO: 1, wherein the promoter is non-native to said SEQ ID NO: 1 and drives over-expression of SEQ ID NO: 1 when transformed into a plant.

11. An isolated or purified DNA molecule comprising a promoter functional in the plant operably linked to SEQ ID NO: 1, wherein the promoter is non-native and drives over-expression of SEQ ID NO: 2 when transformed into a plant.

* * * * *

SEQUENCE LISTING

<160> NUMBER OF SEQ ID NOS: 29

<210> SEQ ID NO 1
<211> LENGTH: 315
<212> TYPE: DNA
<213> ORGANISM: Arabidopsis thaliana

<400> SEQUENCE: 1

| | |
|---|---|
| atgggtaagg acaacaccag aatcctcatg caattttcag ctctcgcgat ggttttaaca | 60 |
| gctgcaataa tggtgaaaga agctacaagc attcccgttt gcaacattga cacaaacgac | 120 |
| ttggcgaaat gccgtccagc cgtcactgga acaaccctc caccaccggg accggactgc | 180 |
| tgcgcagtgg ccagagttgc taatctacaa tgcctctgcc cgtacaagcc ttatctcccc | 240 |
| actgtcggga tagacccatc tagagtcagg cctcttcttg ccaattgtgg tgtaaacagt | 300 |
| ccttcctgtt tctaa | 315 |

<210> SEQ ID NO 2
<211> LENGTH: 330
<212> TYPE: DNA
<213> ORGANISM: Arabidopsis thaliana

<400> SEQUENCE: 2

| | |
|---|---|
| atgatacga acaataccag aactgtgaaa tttgcagctc ttgcaatagt tttagccgcc | 60 |
| ttggtgttga tggaagaacc tacgagcatt accgcatgta acatcaacgc aaaccatctg | 120 |
| gaaaaatgtc gtccagccgt aattggagac aacccgccat ctccaatcaa agagtgttgt | 180 |
| gaactcctcc aagccgctaa tctgaaatgc atctgcagat tcaagtctgt tctccccgtt | 240 |
| ttagcggttt acccatctaa agtccaggct cttctgagca atgtggcct gacaacaatc | 300 |
| cctcctgctt gccaagcttt gaggaactga | 330 |

<210> SEQ ID NO 3
<211> LENGTH: 1374
<212> TYPE: DNA
<213> ORGANISM: Arabidopsis thaliana

<400> SEQUENCE: 3

| | |
|---|---|
| atgtcgcaga gatggagtag aaagaagagt agacttccat tagcgggtct cctctttatt | 60 |
| ctcgttgtca cctttatgat tctcttcaac gagcgtagca ttcagcagat ccatcaccac | 120 |
| gccgcgagtc acactcaaaa tctccgagaa ccttccacgt tcgatttcgt caagcctaat | 180 |
| gttcctcgga ttaactactt gggagctcat ggattctgtt ttgaaaaaaa tgcagaggtt | 240 |
| ttggatagat tcagcaaatg caactcgacg aaagagtaca gtgggaagaa aatcggatgg | 300 |
| gttgacccgt ttgaagacca cccgggtcaa gtaacaaagg aggagcagaa atgtgatgtc | 360 |
| ttttctggga aatgggtctt tgataattca tcatcatacc ctttacacaa ggaatctcag | 420 |
| tgtccttaca tgtccgacca gttggcttgt cagaagcatg taggaagga tttggagtat | 480 |
| cagcattgga gatggcaacc tcatgcctgc aacttgaaga gatggaatgc gatagaaatg | 540 |
| tgggagaagc tgagaggaaa gagattgatg tttgttggag actcgttaaa cagaggccaa | 600 |
| tggatttcaa tggtttgtct cttacagtct gtcattccac gtgacaagca gtctatgtct | 660 |
| cctaacgctc acctcaccat tttcagggct gaggactaca atgccacagt ggagtttctc | 720 |
| tgggcaccgt tgctcgtgga gtcgaattct gatgaccctg ttaatcacag attgagcgag | 780 |
| cggattatcc gacccgattc tgttcttaaa catgcatcaa agtggcaaca tgctgatatt | 840 |
| ctaatcttca acacctactt atggtggaga caagactctg tcaagctccg atggagcagt | 900 |

```
gaagaaaaag ggtcatgcga ggaggtgaag agcgccgagg gaatggagat ggcaatggat      960
agttggggtg attgggttgc taacaatgtc gatccaaaca aaaagcgagt tttcttcgtt     1020
acaatgtctc ctacacatca atggagccga gaatggaacc cgggaagcga aggaaactgc     1080
tacggggaga agaaaccaat agaggaagag agttattggg gaagtgggtc ggacattccg     1140
acaatgagga tggtgaagag agttttggag agattgggac caaaggtctc agttataaac     1200
atcactcagt tgtctgagta tcgaaaagat ggtcatccat cggtgtaccg gaaattctgg     1260
gaacctctaa atgaagaccg gttgaaaaac ccggcatcgt attctgactg tactcattgg     1320
tgtgtacctg gagttcctga tgtctggaat caattgcttt ccattttttt gtga           1374

<210> SEQ ID NO 4
<211> LENGTH: 369
<212> TYPE: DNA
<213> ORGANISM: Triticum aestivum

<400> SEQUENCE: 4
atggctcgtc tcaacagcaa ggctgtggcg gccgccgtgg tcctggcggc ggtggtgctg       60
atgatggccg gcagggaggc ctcggcggcg ctgtcgtgcg gcaggtggac tccaagctc       120 gcgccgtgcg tggcgtacgt gacggggagg gcgtcctcga tcagcaagga gtgctgctcc      180
ggcgtgcagg ggctgaacgg cctggcccgc agcagcccgg accgcaagat agcgtgcagg      240
tgcctcaaga gcctcgccac cagcatcaag tccatcaaca tgggcaaggt ctccggcgtg      300
cccggcaagt gcggcgtcag cgtgcccttc cccatcagca tgtccaccaa ctgcaacaat      360
gtcaactag                                                             369

<210> SEQ ID NO 5
<211> LENGTH: 104
<212> TYPE: PRT
<213> ORGANISM: Arabidopsis thaliana

<400> SEQUENCE: 5

Met Gly Lys Asp Asn Thr Arg Ile Leu Met Gln Phe Ser Ala Leu Ala
 1               5                  10                  15

Met Val Leu Thr Ala Ala Ile Met Val Lys Glu Ala Thr Ser Ile Pro
             20                  25                  30

Val Cys Asn Ile Asp Thr Asn Asp Leu Ala Lys Cys Arg Pro Ala Val
         35                  40                  45

Thr Gly Asn Asn Pro Pro Pro Gly Pro Asp Cys Cys Ala Val Ala
     50                  55                  60

Arg Val Ala Asn Leu Gln Cys Leu Cys Pro Tyr Lys Pro Tyr Leu Pro
65                  70                  75                  80

Thr Val Gly Ile Asp Pro Ser Arg Val Arg Pro Leu Leu Ala Asn Cys
                 85                  90                  95

Gly Val Asn Ser Pro Ser Cys Phe
            100

<210> SEQ ID NO 6
<211> LENGTH: 109
<212> TYPE: PRT
<213> ORGANISM: Arabidopsis thaliana

<400> SEQUENCE: 6

Met Asp Thr Asn Asn Thr Arg Thr Val Lys Phe Ala Ala Leu Ala Ile
 1               5                  10                  15
```

Val Leu Ala Ala Leu Val Leu Met Glu Pro Thr Ser Ile Thr Ala
            20                  25                  30

Cys Asn Ile Asn Ala Asn His Leu Glu Lys Cys Arg Pro Ala Val Ile
         35                  40                  45

Gly Asp Asn Pro Pro Ser Pro Ile Lys Glu Cys Cys Glu Leu Leu Gln
 50                  55                  60

Ala Ala Asn Leu Lys Cys Ile Cys Arg Phe Lys Ser Val Leu Pro Val
 65                  70                  75                  80

Leu Ala Val Tyr Pro Ser Lys Val Gln Ala Leu Leu Ser Lys Cys Gly
                 85                  90                  95

Leu Thr Thr Ile Pro Pro Ala Cys Gln Ala Leu Arg Asn
            100                 105

<210> SEQ ID NO 7
<211> LENGTH: 457
<212> TYPE: PRT
<213> ORGANISM: Arabidopsis thaliana

<400> SEQUENCE: 7

Met Ser Gln Arg Trp Ser Arg Lys Lys Ser Arg Leu Pro Leu Ala Gly
 1               5                  10                  15

Leu Leu Phe Ile Leu Val Val Thr Phe Met Ile Leu Phe Asn Glu Arg
            20                  25                  30

Ser Ile Gln Gln Ile His His Ala Ala Ser His Thr Gln Asn Leu
         35                  40                  45

Arg Glu Pro Ser Thr Phe Asp Phe Val Lys Pro Asn Val Pro Arg Ile
 50                  55                  60

Asn Tyr Leu Gly Ala His Gly Phe Cys Phe Glu Lys Asn Ala Glu Val
 65                  70                  75                  80

Leu Asp Arg Phe Ser Lys Cys Asn Ser Thr Lys Glu Tyr Ser Gly Lys
                 85                  90                  95

Lys Ile Gly Trp Val Asp Pro Phe Glu Asp His Pro Gly Gln Val Thr
            100                 105                 110

Lys Glu Glu Gln Lys Cys Asp Val Phe Ser Gly Lys Trp Val Phe Asp
        115                 120                 125

Asn Ser Ser Tyr Pro Leu His Lys Glu Ser Gln Cys Pro Tyr Met
    130                 135                 140

Ser Asp Gln Leu Ala Cys Gln Lys His Gly Arg Lys Asp Leu Glu Tyr
145                 150                 155                 160

Gln His Trp Arg Trp Gln Pro His Ala Cys Asn Leu Lys Arg Trp Asn
                165                 170                 175

Ala Ile Glu Met Trp Glu Lys Leu Arg Gly Lys Arg Leu Met Phe Val
            180                 185                 190

Gly Asp Ser Leu Asn Arg Gly Gln Trp Ile Ser Met Val Cys Leu Leu
        195                 200                 205

Gln Ser Val Ile Pro Arg Asp Lys Gln Ser Met Ser Pro Asn Ala His
    210                 215                 220

Leu Thr Ile Phe Arg Ala Glu Asp Tyr Asn Ala Thr Val Glu Phe Leu
225                 230                 235                 240

Trp Ala Pro Leu Leu Val Glu Ser Asn Ser Asp Asp Pro Val Asn His
                245                 250                 255

Arg Leu Ser Glu Arg Ile Ile Arg Pro Asp Ser Val Leu Lys His Ala
            260                 265                 270

Ser Lys Trp Gln His Ala Asp Ile Leu Ile Phe Asn Thr Tyr Leu Trp
        275                 280                 285

```
Trp Arg Gln Asp Ser Val Lys Leu Arg Trp Ser Ser Glu Glu Lys Gly
        290                 295                 300

Ser Cys Glu Glu Val Lys Ser Ala Glu Gly Met Glu Met Ala Met Asp
305                 310                 315                 320

Ser Trp Gly Asp Trp Val Ala Asn Asn Val Asp Pro Asn Lys Lys Arg
                325                 330                 335

Val Phe Phe Val Thr Met Ser Pro Thr His Gln Trp Ser Arg Glu Trp
                340                 345                 350

Asn Pro Gly Ser Glu Gly Asn Cys Tyr Gly Lys Lys Pro Ile Glu
                355                 360                 365

Glu Glu Ser Tyr Trp Gly Ser Gly Ser Asp Ile Pro Thr Met Arg Met
        370                 375                 380

Val Lys Arg Val Leu Glu Arg Leu Gly Pro Lys Val Ser Val Ile Asn
385                 390                 395                 400

Ile Thr Gln Leu Ser Glu Tyr Arg Lys Asp Gly His Pro Ser Val Tyr
                405                 410                 415

Arg Lys Phe Trp Glu Pro Leu Asn Glu Asp Arg Leu Lys Asn Pro Ala
                420                 425                 430

Ser Tyr Ser Asp Cys Thr His Trp Cys Val Pro Gly Val Pro Asp Val
                435                 440                 445

Trp Asn Gln Leu Leu Phe His Phe Leu
    450                 455

<210> SEQ ID NO 8
<211> LENGTH: 122
<212> TYPE: PRT
<213> ORGANISM: Triticum aestivum

<400> SEQUENCE: 8

Met Ala Arg Leu Asn Ser Lys Ala Val Ala Ala Ala Val Val Leu Ala
  1               5                  10                  15

Ala Val Val Leu Met Met Ala Gly Arg Glu Ala Ser Ala Ala Leu Ser
                 20                  25                  30

Cys Gly Gln Val Asp Ser Lys Leu Ala Pro Cys Val Ala Tyr Val Thr
             35                  40                  45

Gly Arg Ala Ser Ser Ile Ser Lys Glu Cys Cys Ser Gly Val Gln Gly
         50                  55                  60

Leu Asn Gly Leu Ala Arg Ser Ser Pro Asp Arg Lys Ile Ala Cys Arg
 65                  70                  75                  80

Cys Leu Lys Ser Leu Ala Thr Ser Ile Lys Ser Ile Asn Met Gly Lys
                 85                  90                  95

Val Ser Gly Val Pro Gly Lys Cys Gly Val Ser Val Pro Phe Pro Ile
            100                 105                 110

Ser Met Ser Thr Asn Cys Asn Asn Val Asn
            115                 120

<210> SEQ ID NO 9
<211> LENGTH: 24
<212> TYPE: DNA
<213> ORGANISM: Artificial Sequence
<220> FEATURE:
<223> OTHER INFORMATION: BG646 nested primer

<400> SEQUENCE: 9
acgctgcgga catctacatt tttg                                          24
```

<210> SEQ ID NO 10
<211> LENGTH: 22
<212> TYPE: DNA
<213> ORGANISM: Artificial Sequence
<220> FEATURE:
<223> OTHER INFORMATION: BG647 nested primer

<400> SEQUENCE: 10
cttttcctcc atattgacca tc                                          22

<210> SEQ ID NO 11
<211> LENGTH: 25
<212> TYPE: DNA
<213> ORGANISM: Artificial Sequence
<220> FEATURE:
<223> OTHER INFORMATION: BG648 nested primer

<400> SEQUENCE: 11
catactcatt gctgatccat gtaga                                       25

<210> SEQ ID NO 12
<211> LENGTH: 16
<212> TYPE: DNA
<213> ORGANISM: Artificial Sequence
<220> FEATURE:
<223> OTHER INFORMATION: BG649 degenerate primer
<220> FEATURE:
<221> NAME/KEY: misc_feature
<222> LOCATION: 1, 11
<223> OTHER INFORMATION: n = a, c, t, or g
<220> FEATURE:
<221> NAME/KEY: misc_feature
<222> LOCATION: 7
<223> OTHER INFORMATION: s = g or c
<220> FEATURE:
<221> NAME/KEY: misc_feature
<222> LOCATION: 8, 13
<223> OTHER INFORMATION: w = a or t

<400> SEQUENCE: 12
ngtcgaswga nawgaa                                                 16

<210> SEQ ID NO 13
<211> LENGTH: 16
<212> TYPE: DNA
<213> ORGANISM: Artificial Sequence
<220> FEATURE:
<223> OTHER INFORMATION: BG650 degenerate primer
<220> FEATURE:
<221> NAME/KEY: misc_feature
<222> LOCATION: 3
<223> OTHER INFORMATION: w = a or t
<220> FEATURE:
<221> NAME/KEY: misc_feature
<222> LOCATION: 5, 10
<223> OTHER INFORMATION: n = a, c, t, or g
<220> FEATURE:
<221> NAME/KEY: misc_feature
<222> LOCATION: 8, 13
<223> OTHER INFORMATION: s = g or c

<400> SEQUENCE: 13
tgwgnagsan casaga                                                 16

<210> SEQ ID NO 14
<211> LENGTH: 16
<212> TYPE: DNA
<213> ORGANISM: Artificial Sequence
<220> FEATURE:
<223> OTHER INFORMATION: BG651 degenerate primer
<220> FEATURE:

```
<221> NAME/KEY: misc_feature
<222> LOCATION: 3, 8, 13
<223> OTHER INFORMATION: w = a or t
<220> FEATURE:
<221> NAME/KEY: misc_feature
<222> LOCATION: 5, 10
<223> OTHER INFORMATION: n = a, c, t, or g

<400> SEQUENCE: 14
agwgnagwan cawagg                                              16

<210> SEQ ID NO 15
<211> LENGTH: 16
<212> TYPE: DNA
<213> ORGANISM: Artificial Sequence
<220> FEATURE:
<223> OTHER INFORMATION: BG652 degenerate primer
<220> FEATURE:
<221> NAME/KEY: misc_feature
<222> LOCATION: 1, 8
<223> OTHER INFORMATION: s = g or c
<220> FEATURE:
<221> NAME/KEY: misc_feature
<222> LOCATION: 5, 10, 13
<223> OTHER INFORMATION: n = a, c, t, or g

<400> SEQUENCE: 15
sttgntastn ctntgc                                              16

<210> SEQ ID NO 16
<211> LENGTH: 22
<212> TYPE: DNA
<213> ORGANISM: Artificial Sequence
<220> FEATURE:
<223> OTHER INFORMATION: ACT8 forward primer

<400> SEQUENCE: 16
atgaagatta aggtcgtggc ac                                       22

<210> SEQ ID NO 17
<211> LENGTH: 20
<212> TYPE: DNA
<213> ORGANISM: Artificial Sequence
<220> FEATURE:
<223> OTHER INFORMATION: AT5G55430 forward primer

<400> SEQUENCE: 17
gtacgttgct ttccccaaga                                          20

<210> SEQ ID NO 18
<211> LENGTH: 20
<212> TYPE: DNA
<213> ORGANISM: Artificial Sequence
<220> FEATURE:
<223> OTHER INFORMATION: AT5G55440 forward primer

<400> SEQUENCE: 18
gtggattctc cctctggtga                                          20

<210> SEQ ID NO 19
<211> LENGTH: 20
<212> TYPE: DNA
<213> ORGANISM: Artificial Sequence
<220> FEATURE:
<223> OTHER INFORMATION: AT5G55450 forward primer

<400> SEQUENCE: 19
tgcaacattg acacaaacga                                          20
```

<210> SEQ ID NO 20
<211> LENGTH: 20
<212> TYPE: DNA
<213> ORGANISM: Artificial Sequence
<220> FEATURE:
<223> OTHER INFORMATION: AT5G55460 forward primer

<400> SEQUENCE: 20
cgcaaaccat ctggaaaaat                                               20

<210> SEQ ID NO 21
<211> LENGTH: 20
<212> TYPE: DNA
<213> ORGANISM: Artificial Sequence
<220> FEATURE:
<223> OTHER INFORMATION: LTP4 forward primer

<400> SEQUENCE: 21
atgggtaagg acaacaccag                                               20

<210> SEQ ID NO 22
<211> LENGTH: 23
<212> TYPE: DNA
<213> ORGANISM: Artificial Sequence
<220> FEATURE:
<223> OTHER INFORMATION: LTP5 forward primer

<400> SEQUENCE: 22
atggatacga acaataccag aac                                           23

<210> SEQ ID NO 23
<211> LENGTH: 24
<212> TYPE: DNA
<213> ORGANISM: Artificial Sequence
<220> FEATURE:
<223> OTHER INFORMATION: ACT8 reverse primer

<400> SEQUENCE: 23
gtttttatcc gagtttgaag aggc                                          24

<210> SEQ ID NO 24
<211> LENGTH: 20
<212> TYPE: DNA
<213> ORGANISM: Artificial Sequence
<220> FEATURE:
<223> OTHER INFORMATION: AT5G55430 reverse primer

<400> SEQUENCE: 24
accgctacat cctcgacatc                                               20

<210> SEQ ID NO 25
<211> LENGTH: 20
<212> TYPE: DNA
<213> ORGANISM: Artificial Sequence
<220> FEATURE:
<223> OTHER INFORMATION: AT5G55440 reverse primer

<400> SEQUENCE: 25
cccatcttgc ctaaagacca                                               20

<210> SEQ ID NO 26
<211> LENGTH: 20
<212> TYPE: DNA
<213> ORGANISM: Artificial Sequence
<220> FEATURE:

-continued

```
<223> OTHER INFORMATION: AT5G55450 reverse primer

<400> SEQUENCE: 26
atgggtctat cccgacagtg                                                   20

<210> SEQ ID NO 27
<211> LENGTH: 20
<212> TYPE: DNA
<213> ORGANISM: Artificial Sequence
<220> FEATURE:
<223> OTHER INFORMATION: AT5G55460 reverse primer

<400> SEQUENCE: 27
caagcaggag ggattgttgt                                                   20

<210> SEQ ID NO 28
<211> LENGTH: 23
<212> TYPE: DNA
<213> ORGANISM: Artificial Sequence
<220> FEATURE:
<223> OTHER INFORMATION: LTP4 reverse primer

<400> SEQUENCE: 28
gaaacaggaa ggactgttta cac                                               23

<210> SEQ ID NO 29
<211> LENGTH: 18
<212> TYPE: DNA
<213> ORGANISM: Artificial Sequence
<220> FEATURE:
<223> OTHER INFORMATION: LTP5 reverse primer

<400> SEQUENCE: 29
gttcctcaaa gcttggca                                                     18
```